United States Patent [19]

Nakano et al.

[11] Patent Number: 4,904,660
[45] Date of Patent: Feb. 27, 1990

[54] HISTIDINE DERIVATIVES AS SUPERIOR RENIN INHIBITORS

[75] Inventors: Kohji Nakano; Takashi Fujikura, both of Saitama; Ryuichiro Hara, Tokyo; Masato Ichihara, Tokyo; Yukiko Fukunaga, Tokyo; Masayuki Shibasaki, Tokyo, all of Japan

[73] Assignee: Yamanouchi Pharmaceutical Co., Ltd., Tokyo, Japan

[21] Appl. No.: 160,173

[22] Filed: Feb. 25, 1988

[30] Foreign Application Priority Data

Feb. 27, 1987 [JP] Japan .................................. 62-46454
May 12, 1987 [JP] Japan .................................. 62-115144
Aug. 18, 1987 [JP] Japan .................................. 62-206146
Nov. 16, 1987 [JP] Japan .................................. 62-289017

[51] Int. Cl.$^4$ .................... A61K 31/38; A61K 31/40; A61K 31/41; A61K 31/415; C07D 417/00; C07D 253/00; C07D 413/00; C07D 401; C07D 100; C07D 285/12; C07D 285/14; C07D 513/00; C07D 233/64

[52] U.S. Cl. .................... 514/236.2; 514/226.8; 514/227.2; 514/227.5; 514/227.8; 514/235.8; 514/241; 514/242; 514/245; 514/252; 514/269; 514/272; 514/329; 514/330; 514/331; 514/341; 514/361; 514/362; 514/363; 514/365; 514/370; 514/372; 514/374; 514/378; 514/381; 514/400; 544/55; 544/58.4; 544/58.5; 544/139; 544/182; 544/215; 544/238; 544/331; 544/333; 544/370; 544/405; 546/210; 546/278; 548/128; 548/134; 548/135; 548/136; 548/138; 548/192; 548/194; 548/195; 548/196; 548/200; 548/204; 548/214; 548/243; 548/244; 548/245; 548/246; 548/247; 548/248; 548/249; 548/251; 548/253; 548/233; 548/236; 548/336; 548/344; 548/250

[58] Field of Search .............. 548/336, 344, 233, 236, 548/192, 194, 195, 196, 200, 204, 214, 243, 244, 245, 246, 247, 248, 249, 250, 251, 253, 138, 136, 128, 134, 135; 546/278, 210; 544/139, 55, 58.4, 58.5, 405, 370, 238, 331, 333, 182, 215; 514/374, 365, 370, 372, 378, 235.8, 341, 329, 330, 331, 226.8, 227.2, 227.5, 227.8, 252, 269, 272, 241, 242, 245, 381, 363, 362, 361, 400, 236.2

[56] References Cited

U.S. PATENT DOCUMENTS 4,233,310 11/1980 Fujita et al. .................... 548/344

Primary Examiner—Mary C. Lee
Assistant Examiner—J. Richter
Attorney, Agent, or Firm—Burgess, Ryan & Wayne

[57] ABSTRACT

Novel compounds of the following formula (I) and their salts: A compound of the formula (I)

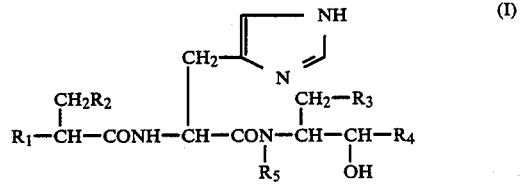

These compounds are expected to be useful for renin inhibitors. Thus, the compounds are useful medical agents, in particular, anti-hypertensive agents.

10 Claims, No Drawings

HISTIDINE DERIVATIVES AS SUPERIOR RENIN INHIBITORS

PRIOR ART AND TECHNICAL PROBLEMS

Renin is an aspartic proteinase which catalyzes a specific hydrolysis of the glycoprotein angiotensinogen to give the decapeptide angiotensin I. A dipeptidylcarboxypeptidase, angiotensin converting enzyme (ACE), then converts it to the octapeptide AII, which, in addition to being an extremely potent vasoconstrictor, is also a promotor of aldosterone release and thereby sodium retention. Aminopeptidases further act on AII to give AIII, which produces effects similar to those produced by AII, but to a lesser extent. This cascade, known as the renin-angiotensin system, is therefore an important area in the regulation of blood pressure and electrolyte homeostasis.

"Renin Inhibitor" inhibits a reaction between rennin and the angiotensinogen, and reduces the formation of angiotensin I, which results in inhibiting the formation of angiotensin II (AII) which produces high blood pressure and also a promotor of aldosterone release. Since renin has remarkable specificity toward its substrate, inhibitors of this enzyme should produce a more direct probe of the renin-angiotensin system. In a limited number of cases, the manipulation of the renin-angiotension system by renin inhibitors (among them substrate analogue inhibitor, peptides derived from the profragment segment, pepstatin/statin-based inhibitors, and other transition-state or intermediate analogues of substrate) has led to blood-pressure lowering. Such recently found renin inhibitors are shown in J. Med. Chem., 28, 1553(1985), J, Med, Chem., 28, 1756(1985), Tokukaisho.61-33152, Tokukaisho.61-122296, Tokukaish.61-236770, 61-275257 and 61-275258.

In order for renin inhibitors to be useful for clinical use, the following are needed.

(1) Strong inhibiting effect to human renin.
(2) Prolongation of the action time which makes them suitable for clinical use.
(3) Superiority of the absorption through intestine.
(4) High specific activity in inhibiting human renin.

Some transition-state analogue (statin-based inhibitors) had an inhibiting effect to some extent, and some peptides having N-terminal and/or C-terminal protecting groups have produced the prolongation of the effect to some extent; however, the above (1) to (4) have not been completely solved in the prior art.

That is, for improving the absorption through intestine, it is believed to provide low molecular compounds, and the research has been proceeding for providing low molecular tripeptide and dipeptide of transition state analogues; however, prior art low molecular transition-state analogues renin inhibitors have lost considerably the activity by the action of proteinase in alimentary canal system. Only the above Tokukaisho 61-236770 describes some renin inhibitor peptide being absorbed to some extent after oral administration, however, in the case of this inhibitor, the specific activity in human renin and the prolongation of the action are not sufficient, and so, further improvement for the activity has been needed. On the other hand, the above Tokukaisho. 61-33152 describes some compounds of the formula, and R6 includes "heteroaryl" as a kind of aryl.

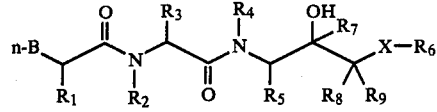

Neverthless, there is not any specific description for the hetero ring. Further, EP Nos. 172347 and 200406 discloses some renin inhibitors such as

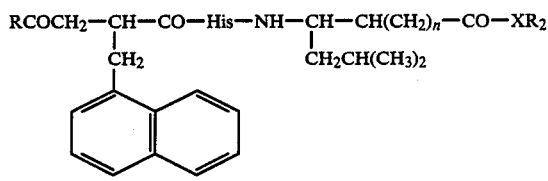

However, the compounds of the present invention (that is the formula (I) compounds) are entirely structurally different from these prior art compounds.

DETAILED EXPLANATION OF THE INVENTION

As a result of investigating and research for providing renin having the above (1) to (4) characteristics, the formula (I) compounds have been found to posses the above (1) to (4) characteristics, and to be clinically useful renin inhibitors. That is, this invention relates to novel compounds of the formula (I) and salts thereof which are useful for medical agents, in particular, antihypertensive agents.

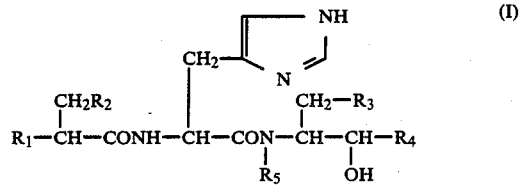

wherein $R_1$ is a lower alkoxycarbonyl group, a lower alkoycarbonylamino group, a group of the formula: —$(CH_2)_n$—A—$R^a$ [wherein n is an integer of 1 or 2; A is a single bond between —$(CH_2)_n$ and $R^a$ (in this case, $R_1$=—$(CH_2)_n$—$R^a$), a lower alkylene group which may be substituted by a hydroxy group(s), or a carbonyl group, $R^a$ is a cyano group, a lower alkyl group, a lower alkynyl group, a cycloalkyl group, a cylcoalkylidene group, an aryl group, an aryloxy group which may be substituted by a halogen atom(s), or a heterocyclic ring group which may be substituted by an amino group(s)]; or a group of the formula: —CONH—B—$R^b$ [wherein B is a single bond, or a lower alkylene; $R^b$ is a hydroxyl group, an aryl group, or a heterocyclic group]; $R_2$ is a phenyl group or a naphthyl group; $R_3$ is a lower alkyl group, cyclohexyl group, or a phenyl group; $R_4$ is a nitromethyl group, a group of the formula: —$COOR^c$ (wherein $R^c$ is a lower alkyl group); or a group of the formula:

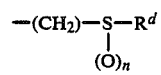

wherein n is 0 or an integer of 1 or 2; $R^d$ is a heterocyclic ring group which may be substituted by a lower alkyl group(s), a carbamoyl-lower-alkyl group(s), or a hydroxy-lower-alkyl group(s)]; and $R_5$ is a hydrogen atom or a lower alkyl group.

In this specification, the term "lower" refers to a straight or branched carbon chain having up to 6 carbon atoms, unless otherwise indicated. Accordingly, concrete examples of the lower alkyl group include methyl, ethyl, propyl, isopropyl, butyl, isobutyl, sec-butyl, tert-butyl, pentyl, isopentyl, neopentyl, tert-pentyl, 1-methylbutyl, 2-methybutyl, 1,2-dimethylpropyl, hexyl, isohexyl, 1-methylpentyl, 2-methylpentyl, 3-methylpentyl, 1,1-diemthylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methyl-propyl groups, etc.

"Carbamoyl lower alkyl" is one obtainable by substituting any hydrogen atom in a "lower alkyl" with "carbamoyl" (—CONH$_2$) and concrete examples of "carbamoyl lower alkyl" include carbamoylmethyl, carbamoylethyl (2- or 1-carbamoylethyl), 3-carbamoylpropyl, 2-carbamoylpropyl, 1-carbamoylpropyl, carbamoylethyl, carbamoylpentyl, carbamoylhexyl, carbamoylbutyl, and their branched lower alkyl derivatives.

"Cycloalkyl" means $C_3$ to $C_7$ ring alkyl, and concrete examples are cyclopropyl, cyclobutyl, cyclopentyl, cyclohexyl, cycloheptyl, etc.

Examples of "lower alkynyl" are ethynyl, propynyl, etc.

Further as the "lower alkoxy group", mention may be made of methoxy, ethoxy, propoxy, isopropoxy, butoxy, isobutoxy, sec-butoxy, tert-butoxy, pentyloxy, (amyloxy), isopentyloxy, tert-pentyloxy, neopentyloxy, 2-methylbutoxy, 1,2-dimethylpropoxy, 1-ethylpropoxy and hexyloxy groups and the like.

Concrete examples of the "aryloxy group" include phenoxy and naphthoxy groups and the like, with particular preference for phenoxy.

As an "aryl group", there are as concrete examples phenyl and naphthyl groups and the like but particularly preferred is phenyl.

An alkylene group preferably has 1 to 6 carbon atoms. Specific examples are methylene, ethylene, methylmethylene (—CH—), trimethylene, tetramethylene, 3,3-dimethyltetramethylene, 4,4-dimethyltetramethylene, 1,1,3-trimethyl-trimethylene, 1,1,2-trimethyl-trimethylene, 1,1,2,2-tetramethylethylene, 1,1-dimethyl-2-ethylethylene, 1,1-diethylethylene.

"Cycloalkylidene" is, particularly, $C_3$ to $C_7$ aliphatic divalent group, and concrete examples are cyclopropylidene, cyclobutylidene, cyclopentylidene, cyclohexylidene, cycloheptylidene, etc.

"Heterocyclic ring group" means, in particular, monocyclic 5- or 6-membered heterocyclic ring. Concrete Examples of "heterocyclic ring" are monocyclic 5- or 6-membered heterocyclic ring which contains oxygen atom(s) and may additionally contain other hetero atom(s) such as tetrahydrofuryl, dihydrofuryl, furyl, dioxolanyl, tetrahydropyranyl, dihydropyranyl, pyranyl, dioxanyl, dioxynyl (namely, heterocyclic ring which contains one or two oxygen atoms), isoxazolidinyl, isooxazolynyl, isooxazolyl, oxazolydinyl, oxazolyl, morpholino, 4H-1,4-oxadinyl, 4H-1,3-oxadinyl, 2H-1,3-oxadinyl, 6H-1,2-oxadinyl, 4H-1,2-oxadinyl, 2H-1,2-oxadinyl (namely, heterocyclic containing one oxygen atom and one nitrogen atom; and further example of "heterocyclic ring" are monocyclic 5- or 6-membered heterocyclic ring which contains nitrogen atom(s) and may additionally contain other hetero atom(s) such as oxygen, sulfur atom(s) and such examples are piperazinyl, pyrrole, pyrrolinyl, pyrrolidinyl, pyridyl, piperidinyl, piperadyl. Examples of other heterocyclic ring groups are thienyl, thiopyranyl, etc. (namely, S-atom containing heterocyclic), thiazolyl, iso-thiazolyl, thiadinyl, etc. (namely, S- and N-atoms containing heterocyclic). Concrete examples of heterocyclic in the case of $R^d$ are, in particular, $C_5$ to $C_6$ N-atom containing heterocyclic which contains further O-atom and/or S-atom such as pyrrolyl, pyrrolinyl, pyrrolidinyl, pyridyl, dihydropyridyl, piperidyl, pyrazolyl, pyrazolinyl, pyrazolidinyl, imidazolyl, imidazolynyl, imidazodinyl, pyradinyl, piperadinyl, pyrimidinyl, pyridadinyl, triazinyl, tetrazolyl, etc. ($N_1$ to $N_4$ containing heterocyclic), oxazolyl, oxazolidinyl, isoxzoly, isooxazolinyl, isooxazolidinyl, etc. (heterocyclic containing one oxygen atom and one nitrogen atom), thiazolyl, thiazolinyl, thiazolidinyl, isothiazolyl, isothiazolinyl, isothiazolinyl, 1,3,4-thiadiazolyl, 1,2,4-tiadiazolyl, 1,2,5-thiadiazolyl, etc. (one or two nitrogen atom(s)-containing and further one S-containing heterocyclic). Further examples of 5- or 6-membered heterocyclic ring are tetrahydrofuryl, dihydrofuryl, furyl, dioxolanyl, dioxolyl, tetrahydropyranyl, dihydrppyranyl, pyranyl, dioxanyl, ioxynyl (one or two oxygen atom(s)-containing heterocyclic ring group), thienyl, thiopyranyl (sulfur atom-containing heterocyclic ring group), thiazolyl, isothizolyl, thiadinyl, etc. (sulfur and nitrogen atoms-containing heterocyclic ring group).

The present invention includes the salts of compounds (I), and examples of such salts include acid addition salts with organic acids such as mineral acids (e.g. hydrochloric, hydrobromic, hydroiodic, sulfuric, nitric and phosphoric acids and the like) and with various organic acids such as formic, acetic, oxalic, citric, succinic, fumaric, maleic, malic, tartaric, methanesulfonic and ethanesulfonic acids and the like. Acidic amino acid such as aspartic acid, glutamic acid are also listed for forming a salt.

Some compounds according to the invention can evidently have various isomers such as optical isomer, diastereoisomer and geometrical isomers. The present invention includes isolated isomers and any mixtures thereof. In particular, the formula (I) compounds have 3 to 4 assymetric carbon atoms, and have optical isomers.

As the salts of the present compounds, there are also listed a salt with alkali (sodium, potassium, etc.), alkali earth metal (magnesium, calcium, etc.), and with organic base (diethylamine, triethylamine, diethanolamine, cyclohexylamine).

The formula (I) compounds of this invention can be prepared by, for example, the following processes.

PROCESS 1:

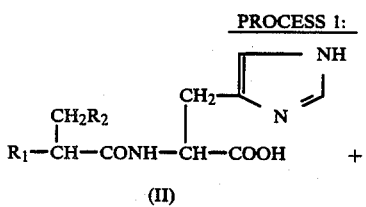

(II)

-continued
PROCESS 1:

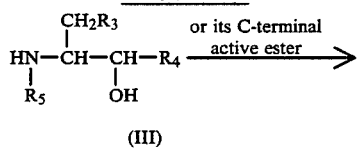

The formula (I) compound

The formula (I) compounds can be prepared by reacting the formula (II) compound with the formula (III) compound, and, if necessary, by removing the protective group.

As the formula (II) compounds, there may be used a free acid or a N-hydroxylamine-active ester. Coupling method in the presence of condensing agent can be applied. Active esters such as N-nitrophenol-active ester (N-nitrophenol-active ester, etc.), N-hydroxylamine-active ester (N-hydroxysuccinimide-active ester, 1-hydroxybenzotriazole-active ester, etc.), carbonic acid mono-alkyl ester, mixed-acid (organic acid) anhydride, mixed-phosphoric acid-active ester (diphenyl phosphoryl chloride and N-methylmorpholine are used), acid azide (prepared by acid hydrazide and nitrous acid), acid chloride, acid bromide, etc. (namely, acid halide, acid anhydride can be also used as C-terminal active compound.

As coupling agent in the case of the coupling method, N,N'-dicyclohexylcarbodiimide, carbonyldimiidazole, diphenylphosphoryl azide (DPPA), etc, are used. The reaction can be usually carried out in the presence of a solvent, under cooling or at room temperature. As the solvent, there may be used organic solvent which does not take part in the reaction (for example, dimethylformamide, dimethylacetoamide, dioxane, tetrahydrofuran, ether, dichloromethane, dichloroethane, chloroform, carbon tetrachloride, dimethoxymethane, dimethoxyethane, ethyl acetate, benzene, acetonitrile, dimethylsulfoxide), or a mixture of these organic solvent. A cetain kind of the active ester may or must be reacted under anhydrous or dry condition. It may be preferable to use N-methylmorpholine, triethylamine, trimethyl amine, for a smooth reaction. That is, the presence of such base may result in a smooth reaction. Axide method or coupling method using diethylphosphorylcyanide, etc. are most preferable, in view of problems of protective groups and racemization. Protective groups are removed after the reaction, if they are used.

As a protective group for carboxyl, there may be used preferably, ester residue used usually in the field of peptide synthesis (benzyl, p-nitrobenzyl, diphenylmethyl (benzohydryl), trityl, etc. (namely, substituted benzyls), tert-butyl, methyl, ethyl, etc. (namely, lower alkyls), phenacyl, 4-picolyl, cyclohexyl, etc. As a protective group for imidazolyl, there may be used benzyl, substituted benzyl as above, tert-butyl, etc.

Removal of the protective groups can be conducted by usual manner.

PROCESS 2:

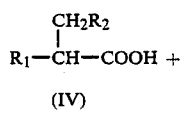

-continued
PROCESS 2:

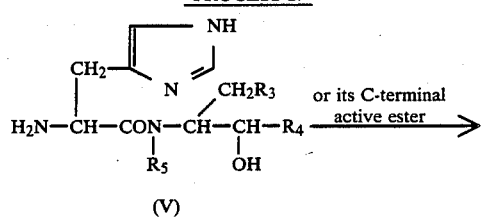

The formula (I) compound

The formula (I) compounds of the present invention can also be prepared by reacting the formula (IV) compound and the formula (V) compound, and, if necessary, by removing the protective group.

The reaction conditions, etc. are the same as in Process 1.

Other Processes:

According to the kind of the subtituent in the formula (I) compound, there any be used various methods. For example, ester derivatives can be made by reacting carboxylic acid or its reactive derivative with lower alcohol or lower alkyl halide (namely, alcohol-reactive ester). [usual esterification]; and free carboxylic acid can be prepared by a usual hydrolysis reaction to ester derivatives.

In the case of $R_1$ having $>N-CO-$ portion, the corresponding carboxllic acid or its C-terminal active ester may be used as a starting material, which is reacted with an amide derivative based upon the $R_1$ group.

The formula (I) compounds having lower alkanoyl portion may be prepared by using the corresponding hydroxy derivative or its reactive derivative as a starting material, which is reacted with lower alkanecarboxylic acid or its reactive derivative.

In the case of $R_4$ being $-CH_2SR^d$, the following reaction method may be used.

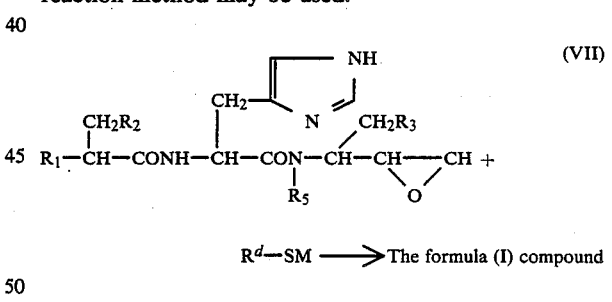

$R^d-SM \longrightarrow$ The formula (I) compound

That is, in this case, the formula (I) compound may be prepared by reacting the formula (VI) compound and the formula (VII) compound.

M represents hydrogen or alkali methal atom; and examples of alkali metal are sodium, potassium, etc. This reaction can be carried out, preferably, in a solvent which does not take part in the reaction, and examples of such solvent are N,N-dimethylformamide, dimethylsulfoxide, ether, tetrahydrofuran, dioxane, methanol, ethanol, iso-propanol, acetone, methylethylketone, dichloromethane, ethylene chloride, chloroform, carbon tetrachloride, etc. (organic solvents), water, and a mixture of water and an organic solvent.

In the case of using mercaptane compound as the formula (VI) compound, it is preferred to carry out the reaction in the presence of a base, and examples of the base are triethylamine, trimethylamine, potassium carbonate, sodium carbonate, potassium hydroxide, etc.

(organic bases and inorganic bases). The reaction temperature is not particularly limited, and according to the kinds of the starting materials, etc., the reaction can be conducted under cooling, at room temperature, or under heating.

In the case of $R_1$ having the —COCH$_2$— portion, the present compounds can be prepared by the corresponding carboxylic acid or its derivative with the corresponding halide or sulfonate X—CH$_2$—: X=halogen, or p-toluenesulfonyloxy, methanesulfonyl (organic sulfonic acid residue) in a conventional manner.

In the case of the present compounds having thioether portion, a usual thioether-formation reaction (e.g. a reaction between the corresponding mercaptane (—SH) compound or its alkali metal derivative and the corresponding halide or sulfonate can be used.

The compounds of the present invention can be used as they are, in a fee state, or as salts thereof. Isolation and purification can be performed by conventional chemical operations such as extraction, crystallization, recrystallization, various chromatography techniques, etc.

In the compounds of the present invention, racemates, optically active forms, diastereoisomers and the like may be present singly or in admixture. Stereochemically pure isomers can be obtained using appropriate raw compounds or by conventional racemic resolution [for example, by treatment with conventional optically active acid (tartaric acid, etc.) followed by optical resolution, etc.] A mixture of diastereoisomers can be separated in a conventional manner, for example, by fractional crystallization, chromatography, etc.

(The effects of the compounds of this invention)

The formula (I) compounds and their salts have strong inhibiting-activity specific to renin, and also achieve prolongation of the action time which is suitable for clinical administration as well as superiority of the absorption through intestine. Accordingly, the compounds of this invention are useful for treating and preventing high blood pressure, in particular, renin-angiotensin based high blood pressure. The superior effects of the present compounds have been proved by the following experiment.

(1) Inhibiting effect to human plasma renin.

Into human plasma (250 μl) having 0.5 ng/ml/hr (37° C.)-angiotensin I forming activity was added 225 μl of an enzyme-inhibitor (BAL, 8-hydroxysulfate, pH4.6) and 25 μl of a solution of the test compound in dimethylsulfoxide, and the mixture was stirred. Some portion of the stirred mixture was subjected to incubation at 37° C. for 2 hours, and the rest of the mixture was left at 4° C. Taking 100 μl of each of the mixtures, by measuring the difference of the angiotensin I forming amount by radio-immunoassay at 37° C. and 4° C., the 50% inhibiting concentration IC50 (M) was calculated. Some data obtained are shown below.

| Ex. No. | $R_1$ | $R_2$ | $R_3$ | $R_4$ | $IC_{50}$/human plasma |
|---------|-------|-------|-------|-------|------------------------|
| Ex. 40 | morpholine-N—CO—CH$_2$— | naphthyl | H | COOCH(CH$_3$)$_2$ (cyclohexyl) | $4 \times 10^{-9}$ |
| Ex. 7 | morpholine-N—CO—CH$_2$— | naphthyl | H | CH$_2$—S—TZ (cyclohexyl), Tz 1-methyl-5-tetrazolyl | $5 \times 10^{-10}$ |
| Ex. 9 | (CH$_3$)$_3$COCONH | phenyl | H | CH$_2$—S—TZ (cyclohexyl) | $4 \times 10^{-9}$ |

Compositions containing one or more compounds (I) or salts thereof as effective components can be prepared as tablets, powders, granules, granulates, capsules, pills, liquid, injections, suppositories, ointments, haps, etc., using conventional carriers, excipients, etc., and other additives, and can be administered orally (including sublingually) or parenterally.

The carriers and excipients for medical preparations include solid or liquid non-toxic pharmaceutical substances. Examples of such substances are lactose, magnesium stearate, starch, talc, gelatin, agar, pectin, gum arabic, olive oil, sesame oil, cacao butter, ethylene glycol, etc. and other substances ordinarily used.

Clinical dosage of the compounds of the present invention may be appropriately determined depending upon condition, body weight, age, sex, etc. of the patient to be treated, but is generally 0.5 to 5000 mg daily for an adult, administered in one does or two sub-doses. (Oral: 1–500 mg, Parenteral: 0.5–100 mg).

The present compounds having peptide characteristics can be usually administered as a pharmaceutical composition such as tablets, pills, capsules, etc. prepared by using carriers or excipients usually used for peptide-pharmaceutical composition for oral or parenteral administration such as injection.

Reference example compounds were prepared by conventional manners (Reference Example)

1. (2RS,3S)-3-N-t-butoxycarbonylamino-5-methyl-1-(1-methyl-5-tetrazolylthio)-2-hexanol.

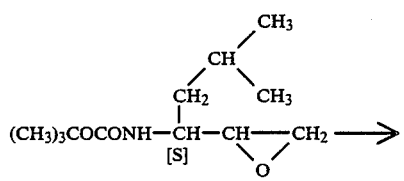 →
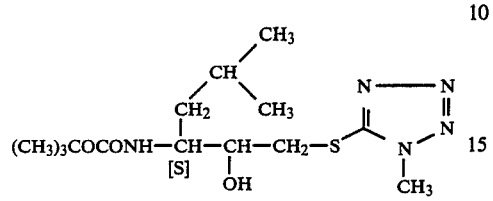
(m/z): 346 (M+ + 1), 290, 246
(KBr) cm⁻¹: 3368, 1688, (CDCl₃, TMS
δ ppm: 0.94(d, 6H, 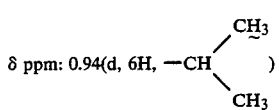)
1.42(s, 9H, t-BuO—)
3.40(d, 2H, 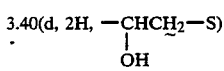)
3.96(s, 3H, 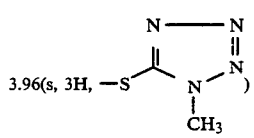)
2.–5.
In similar way to 1 above, the following were prepared.
2. (2RS,3S)-3-N-t-butoxycarbonylamino-5-methyl-1-(2-thiazolylthio)-2-hexanol.
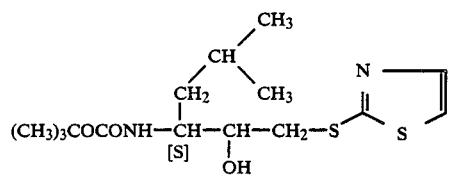
3. (2RS,3S)-3-N-t-butoxycarbonylamino-5-methyl-1-[(5-methyl-1,3,4-thiadiazole-2-yl)thio]-2-hexanol.
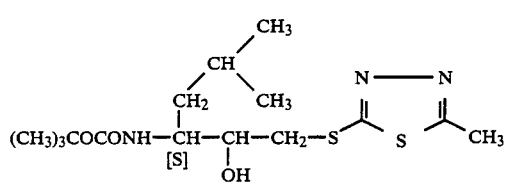
4.
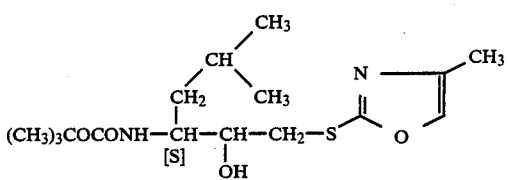
5.
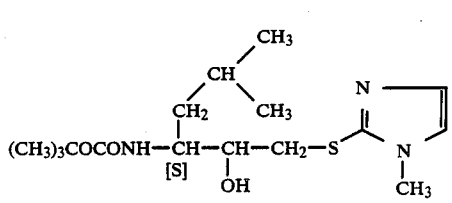
6.
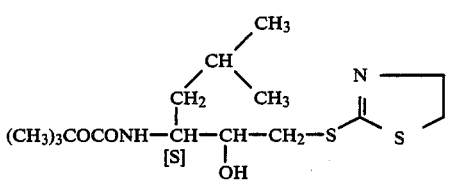
7.
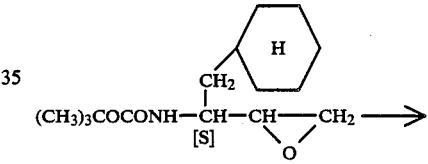
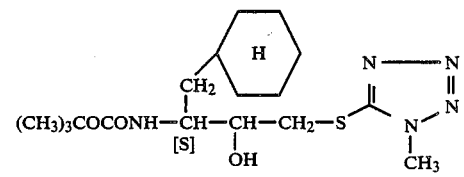
8.
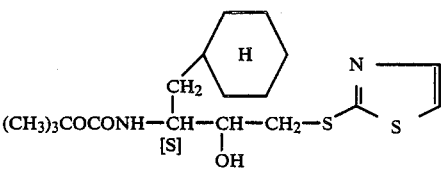
9.
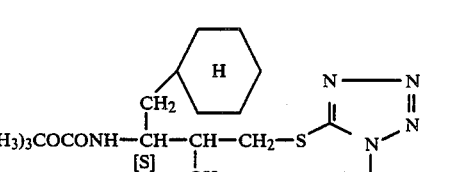
11.

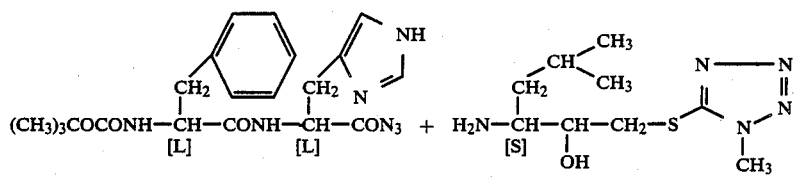

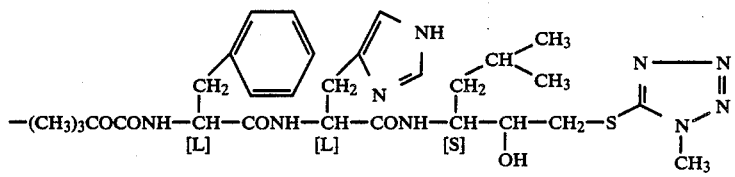

12.

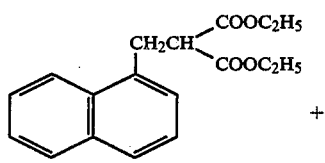

+

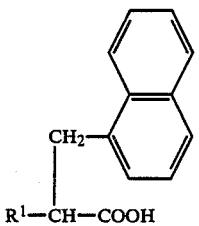

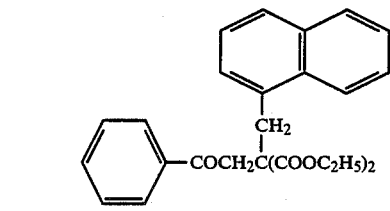

13.

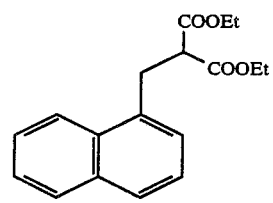

14. 2-(1-naphtylmethyl)-2-[2-oxo-2-(tetrahydropyran-4-yl) ethyl]malonic acid diethyl ester
15. 2-2[2-(3-thienyl)-2-oxoethyl[-2-(1-naphtylmethyl-malonic acid diethyl ester
16. 2-[2-(2-thienyl)-2-oxoethyl]-2-(1-naphtylmethyl)-malonic acid diethyl ester
17. 2-(3-methyl-2-oxobutyl)-2-(naphtylmethyl)malonic acid diethyl ester
18. 2-(!-naphtylmethyl)-4-phenyl-4-oxobutyric acid
19.

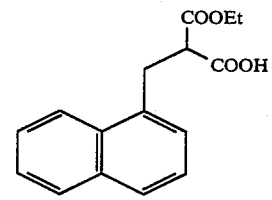

(4-cyclohexyl-2-(1-naphtylmethyl)-4-oxobutyric acid)

20. 4-cyclohexyl-2-(1-naphtylmethyl)-4-oxobutyric acid
21. 2-(1-naphtylmethyl)-4-oxo-4-(tetrahydropyran-4-yl)-butyric acid
22. 4-(3-thienyl)-2-(1-naphtylmethyl)-4-oxobutyric acid
23. 4-(2-thienyl)-2-(1-naphtylmethyl)-4-oxobutyric acid
24. 5-methyl-2-(1-naphtylmethyl)-4-oxohexanoic acid
25. 2-(1-naphtylmethyl)malonic acid monoethylester

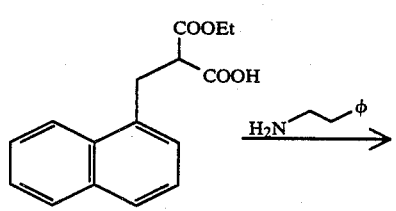

26.

27.
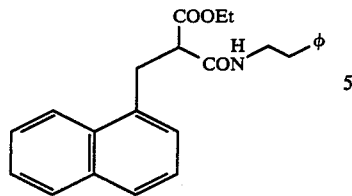
28.
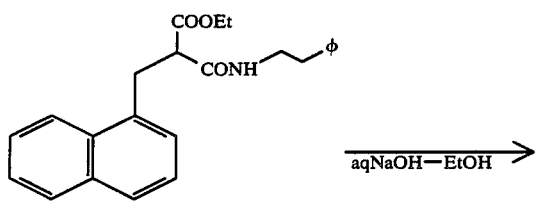 aqNaOH—EtOH →
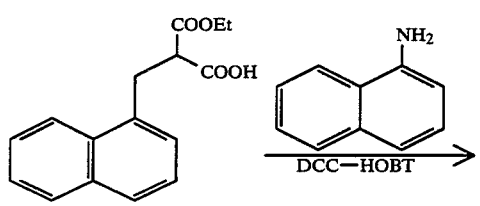
29.
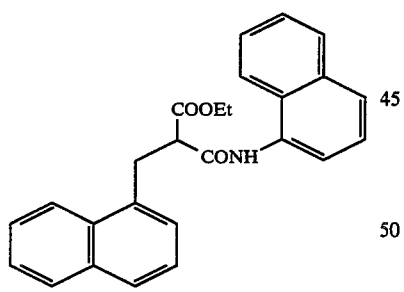 DCC—HOBT →
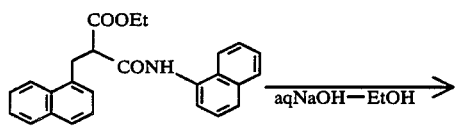
30.
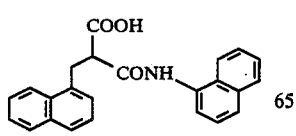 aqNaOH—EtOH →
31.
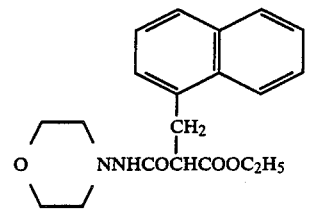
32.
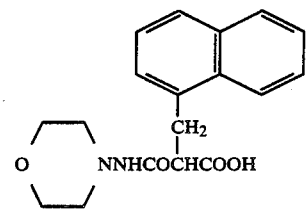
33.
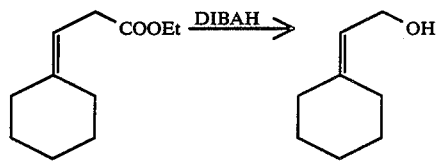 DIBAH →
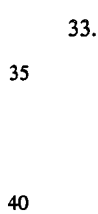
34.
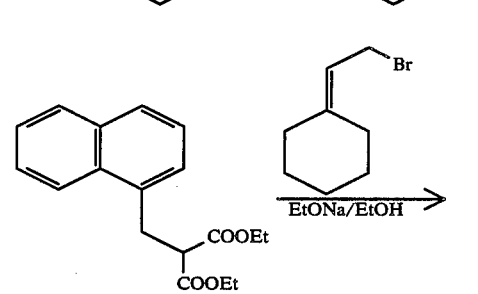 EtONa/EtOH →
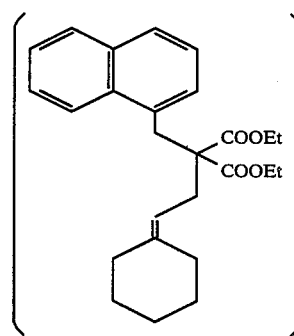

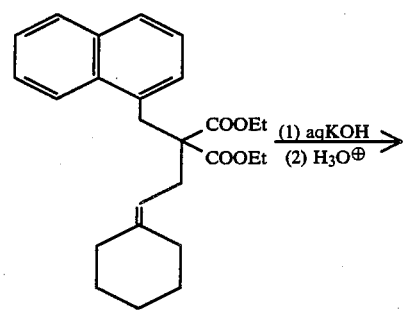

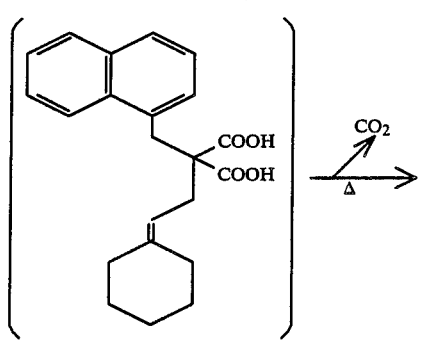

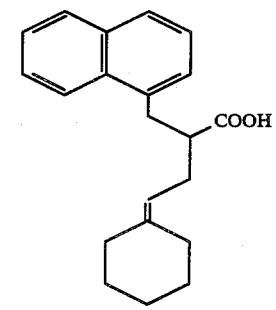

35.

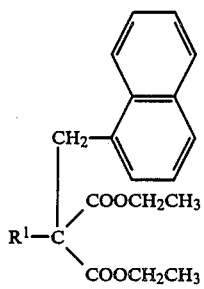

36. 2-3(3-propagyl)-2-(1-naphthylmethyl)malonic acid 37. 2-[-2-(1,3-dioxolan-2-yl)ethyl]-2-(1-naphtylmethyl) malonic acid diethyl ester

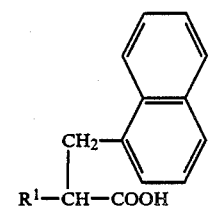

28. 2-(1-naphthylmethyl)-4-pentinic acid
29. 4-(1,3-dioxolan-2-yl)-2-(1-naphtylmethyl)butyric acid
30. (2RS,3S)-3-amino-5,5-dimethyl-2-hydroxyhexanoic acid

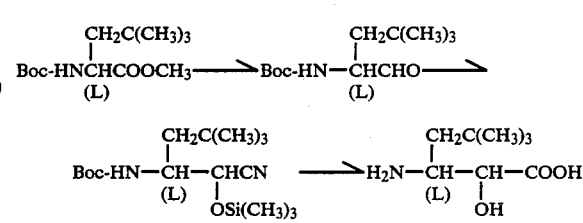

31.–33.

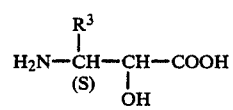

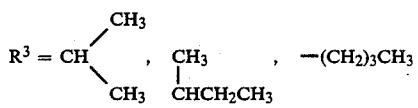

34. (2RS,3S)-3-amino-5,5-dimethyl-2-hydroxyhexanoic acid iso-propyl ester

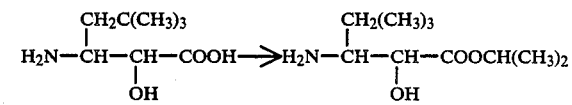

35.–38.

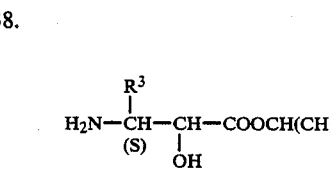

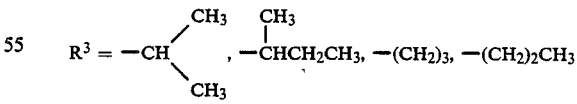

39. (2RS,3S)-3-amino-2-hydroxy-4-cyclohexyl-butyric acid
40. (2RS,3S)-3-amino-2-hydroxy-4-cyclohexyl-butyric acid iso-propyl ester
41. (2RS,3S)-3-amino-2-hydroxy-4-cyclohexyl-butyric acid methyl ester
42. 4-(p-fluorophenoxy)-2-(1-naphthylmethyl)butyric acid
43. (2RS,3S)-3-N-t-butoxycarbonylamino-4-cyclohexyl-1-(1-methyl-5-tetrazolylthio)-2-butanol 1.4ml of triethylamine (10 millimole) was added to a solution of 2.29 g (10 millimole) of 3-t-butoxycarbonyl-amino-4-cyclohexyl-1,2-oxobutan and 1.16 g (10 millimole) of 1-methyl-5-mercaptotetrazole in 20 ml of tetrahydrofuran, and the mixture was stirred overnight at room temperature. To the reaction mixture was added 100 ml of ethyl acetate, and the mixture was washed with water, dried over magnesium sulfate, and concentrated under reduced pressure. To the residue was added ether-n-hexane to give 1.5 g of white powder of the desired compound.

Melting point: 129°-136° C.
IR (KBr) cm$^{-1}$: 3356,2936, 1688, 1530, 1178
NMR (CDCl$_3$): 1.42(s, 9H, t-BuO-), 3.38, 3.93

In similar way to 43 above, the following were prepared.

44. (3S)-1-(benzothiazolylthio)-3-t-butyloxycarbonyl-amino)-1-(2-benzothiazolylthio)-4-cyclohexyl-2-butanol
45. (3S)-3-t-butyloxycarbonylamino-4-cyclohexyl-1-[(5-methyl-1,3,4-thiadiazol-2-yl)thio]-2-butanol
46. (3S)-3-t-butoxycarbonylamino-4-cyclohexyl-1-(2-pyrimidinylthio)-2-butanol
47. (3S)-3-t-butoxycarbonylamino-4-cyclohexyl-1-(1,2,3-thiadiazol-5-ylthio)-2-butanol
48. (3S)-3-t-butoxycarbonylamino)-4-cyclohexyl-1-(1-ethyl-5-tetrazolyl)thio-2-butanol
49. (3S)-3-[(N-t-butoxycarbonyl-L-histidyl)amino]-4-cyclohexyl-1-(2-thiazolylthio)-2-butanol
50. (3S)-3-[N-t-butoxycarbonyl-L-histidinyl]amino)-4-cyclohexyl-1-[(5-methyl-1,3,4-thiadiazol-2-yl)-thio]-2-butanol
51. (3S)-3-[(N-t-butoxycarbonyl-L-histidyl)amino)]-4-cyclohexyl-1-(2-pyrimidinylthio)-2-butanol
52. (3S)-3-[(N-t-butoxycarbnoyl-L-histidyl)amino]-4-cyclohexyl-1-1-(1,2,3thiadiazol-5-ylthio)-2-butanol
53. (3S)-3-[(N-t-butoxycarbonyl-L-histidyl]amino)]-4-cyclohexyl-1-[(1-ethyl-5-tetrazolyl)thio]-2-butanol
54. (3S)-[N-t-butoxycarbonyl-L-histidyl)]amino]-4-cyclohexyl-1-[(1-methyl-5-tetrazolyl)sulfonyl]-2-butanol
55. (3S)-N-t-butoxycarbonylamino)-4-cyclohexyl-1-[(1-methyl-5-tetrazolyl)sulfonyl]-2-butanol
56. (3S)-3-(N-t-butoxycarbonylamino)-5-methyl-1-nitro-2-hexanol

EXAMPLE 1

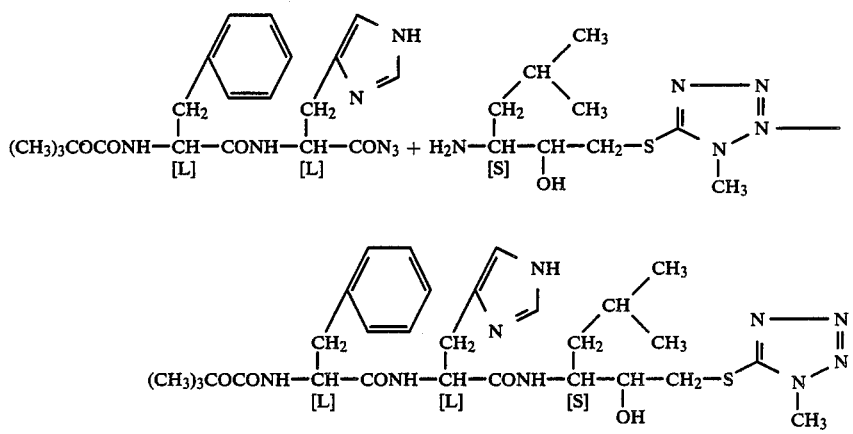

(2RS,3S)-3-(N-t-butoxycarbonyl-L-phenylalanyl-L-histidylamino)-5-methyl-1-[(1-methyl-5-tetrazolyl)-thio]-2-hexanol-t-butoxycarbonyl-L-phenylalanyl-L-histidyl-hydrazide (416 mg, 1 millimole) was dissolved in 10 ml of dimethylformamide, and the obtained solution was cooled to −10 ° C., and after adding thereto 0.84 ml of 4N/HCl/dioxane and 0.2 ml of iso-amyl nitrite while stirring, the mixture was stirred for 30 minutes at −30° C., and 0.45 ml of N-methylmorpholine was added to the mixture while cooling at −40° C.

On the other hand, 5 ml of 4N-HCl/dioxane was added to 345 mg of 3-N-t-butoxycarbonylamino-5-methyl-1-(1-methyl-5-tetrazolylthio)-2-henanol, and the mixture was stirred for 1 hour at room temperature. The reaction solution was concentrated under reduced pressure to dryness, and the residue was dissolved in 10 ml of dimethylformamide. This solution was added to the above reaction mixture, and the obtained mixture was stirred overnight in ice-room.

To the reaction solution was added 100 ml of ethyl acetate, and after washing with aqueous NaHCO$_3$ and water, the mixture was dried over magnesium sulfate, and concentrated under reduced pressure. To the obtained residue was added chloroform, and the desired compound was obtained as white powder (75 mg).

Rf=0.17 (chloroform;methanol=5:1)
Mass spectrum (m/z): 630 (M$^+$ +1)
I.R. (KBr) cm$^{-1}$: 3312, 1698, 1660, 1642

EXAMPLE 2

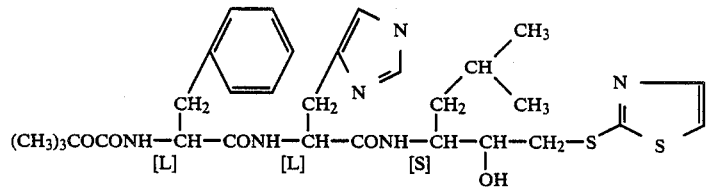

In similar manner to Example 1, (2RS,3S)-3-(N-t-butoxycarbonyl-L-phenylalanyl-L-histidylamino)-5-methyl-1-(2-thiazolylthio)-2-hexanol was obtained.
Rf=0.58 (chloroform:methanol=5:1)
Mass spectrum (m/z): 631 M++1)

I.R. (KBr) cm⁻¹: 3316, 1698, 1644, 1537

EXAMPLE 3

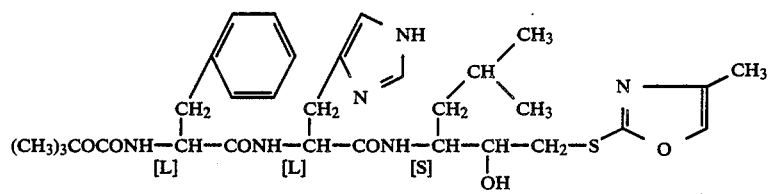

In similar manner to Example 1, (2RS,3S)-3-(N-t-butoxycarbonyl-L-phenylalanyl-L-histidylamino)-5-methyl 1-(4-methyloxazole-2-yl)thio-2-hexanol was
Rf=0.60 (chloroform:methanol:5:)

Mass spectrum (m/z): 629 (M++1)
I.R. (KBr) cm⁻¹: 3328, 1696, 1646, 1522, 1170

EXAMPLE 4

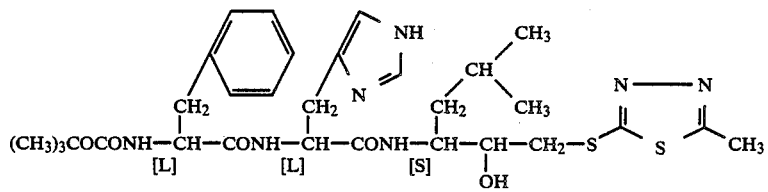

In similar manner to Example 1, (2RS,3S)-3-(N-t-butoxycarbonyl-L-phenylalanyl-L-histidylamino)-5-methyl-1-[(5-methyl-1,3,4-thiadiazol-2-ylthio]-2-hexanol was Rf=0.41 (chloroform:methanol=5:1)
Mass spectrum (m/z): 646 (M++1)
I.R. (KBr) cm⁻¹: 3312, 1698, 1663, 1642, 1530

EXAMPLE 5

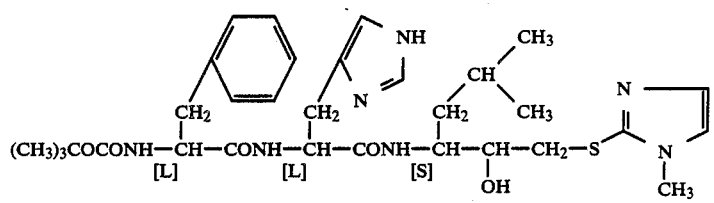

In similar manner to Example 1, (2RS,3S)-3-(N-t-butoxycarbonyl-L-phenylalanyl-L-hisitidylamino)-5-methyl-1-[(1-methylimidazol-2-yl)thio]-2-hexanol was obtained.
Rf=0.55 (chloroform;methanol+5:1)
Mass spectrum (m/z): 628 (M++1)
I.R. (KBr) cm⁻¹: 3324, 1654, 1522

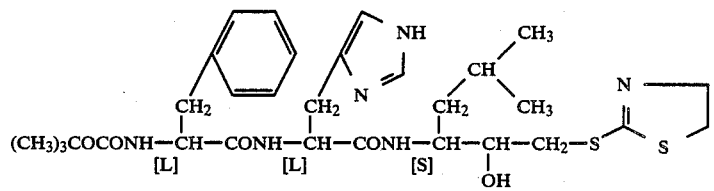

In similar manner to Example 1, was obtained (2RS,3S)-3-(N-t-butoxycarbonyl-L-phenylalanyl-L-histidylamino)-5-methyl-1-[(2-thiazolin-2-yl)thio]-2-hexanol.

Rf=0.62 (chloroform:methanol=5:1)
Mass spectrum (m/z): 633(M++1)
I.R.(KBr): cm⁻¹: 3328, 1668, 1558

EXAMPLE 7

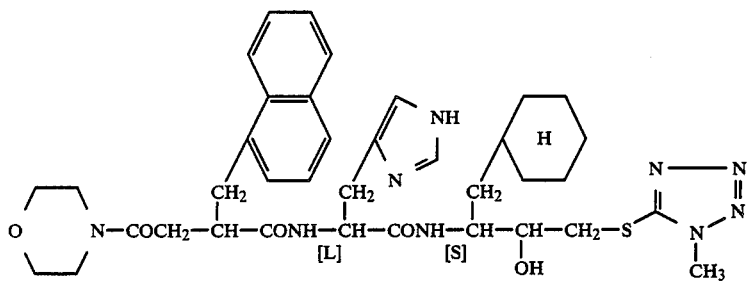

(2RS,3S)-3-[N-[1,4-dioxo-4-morpholino-2-(1-naphthyl-methyl)butyl-L-histidylamino)]-4-cyclohexyl-1-(1-methyl-5-tetrazolylthio)-2-butanol.

To 260 mg of (2RS,3S)-3-N-[(N-t-butoxycarbonyl-L-histidyl)amino]-4-cyclohexyl-1-(-methyl-5-tetrazolyl-thio)-2-butanol (0.5 millimole), was added 5 ml of 4N-HCl/dioxane, and after stirring the mixture for 1 hour at room temperature, the mixture was concentrated under reduced pressure to dryness. To the residue, was added 160 mg of 3-morpholinocarbonyl-2-(1-naphthyl-methyl)propionic acid and 5 ml of dimethylformamide, the mixture was stirred while ice-cooling. To the mixture was added 0.13 ml of diphenylphosphoryl azide and 0.21 ml of triethylamine, and the mixture was stirred overnight at room temperature. To the reaction mixture was added 50 ml of ethyl acetate, and the mixture was washed with aqueous NaHCO$_3$ and water, dried over magnesium sulfate, and concentrated under reduced pressure. The residue was subjected to silica gel chromatography, and the fraction containing the desired compound was concentrated. To the residue was added ether to give 70 mg of white powder of the aimed compound.

RF=0.50 (chloroform:methanol=5:1)
Mass spectrum (m/s): 732 (M$^+$+1), 523
I.R. (KBr) cm$^{-1}$: 3328, 1652, 1450, 1116

EXAMPLE 8

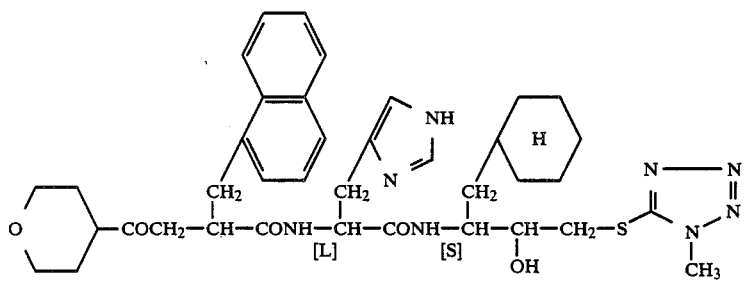

In similar manner to Example 1, was obtained (2RS, 3S)-4-cyclohexyl-3-N-[N-[1,4-dioxo-2-(1-naphthylme-thyl)-4-(tetrahydropyran-4-yl)butyl]-L-histidylamino]-1-(1-methyl-5-tetrazoylthio)-2-butanol.

Rf=0.55 (chloroform:methanol=5:1)
Mass spectrum (m/z): 731 (M$^+$+1)
I.R. (KBr) cm$^{-1}$: 3328, 1705, 1660

EXAMPLE 9

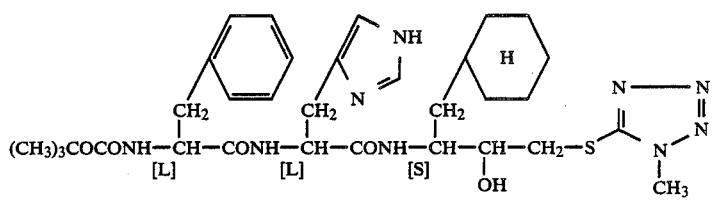

A solution of 416 mg (1 millimole) of t-butoxycarbonyl-L-phenylalanyl-L-histidine hydrazide and 10 ml of dimethylformamide was cooled to −40° C., and after adding thereto 4N-HCl-dioxane (0.84 ml) and 0.2 ml of isoamyl nitrite, the mixture was stirred from 30 minutes at −20°–30° C. After cooling the mixture to −40° C., N-methylmorpholine was added to the mixture. On the other hand, to 385 mg of 3-(N-t-butoxycarbonyl-amino)-4-cyclohexyl-1-(1-methyl-5-tetrazoylthio)-2-butanol was added 5 ml of 4N-HCl/dioxane, and the mixture was stirred at room temperature overnight. The reaction solution was concentrated under reduced pressure, and the residue was dissolved in 10 ml of dimethylformamide. To this solution was added the above reaction solution, and the mixture was stirred in ice-room overnight. To the reaction solution was added 100 ml of ethyl acetate; and the mixture was washed with aqueous NaHCO$_3$ and water, dried over magnesium sulfate, and concentrated under reduced pressure. The residue was subjected to column chromatography and the fraction containing the desired compound was concentrated. To the residue was added ether to give 110 mg of white powder of the desired compound.

Rf=0.48 (chloroform:methanol=5:1)

Mass spectrum (m/z): 670 (M++1)
I.R. (KBr) cm⁻¹: 3328, 1696, 1662, 1642, 1528, 1172

EXAMPLE 10

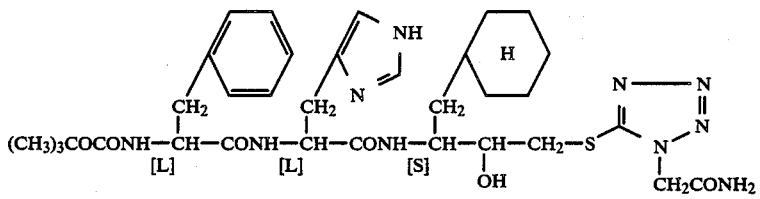

In similar manner to Example 9, was obtained (2RS,3S)-3-(N-t-butoxycarbonyl-L-phenylalanyl-L-histidylamino)-4-cyclohexyl-1-(1-carbamoylmethyl-5-tetrazolylthio)-2-butanol.
Rf=0.27 (chloroform:methanol=5:1)
Mass spectrum (m/z): 713 (M++1)
I.R. (KBr) cm⁻¹: 3328, 1696, 1664, 1642, 1170

EXAMPLE 11

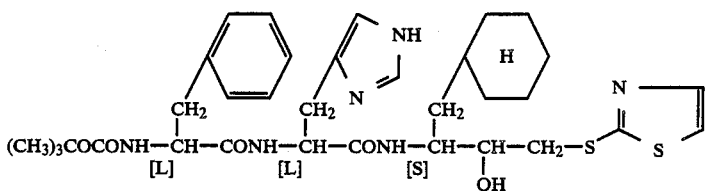

In similar manner to Example 9, was obtained (2RS,3S) -3-(N-butoxycarbonyl-L-phenylalanyl-L-histidylamino)-4-cyclohexyl-1-(2-thiazolylthio)-2-butanol.
Rf=0.54 (chloroform:methanol=5:1)
Mass spectrum (m/z) 671 (M++1)
I.R. (KBr)cm⁻¹: 3336, 1696, 1646, 1528, 1170

Example 12

(2RS,3S) 3-[N-[2-(R,S)-t-butoxycarbonylamino-3-(1-naphthyl)propionyl]-L-histidyl]amino-2-hydroxy-4-cyclohexylbutyric acid iso-propyl ester (R¹: t-butoxycarbonylamino, R²: iso-propoxy) 4N-HCl/dioxane solution was added to 290 mg of N-Boc histidinyl-(2RS,3S)-3-amino-2-hydroxy-4-cyclohexyl butyric acid iso-propyl ether, and the mixture was stirred for 1 hour at room temperature. The reaction solution was concentrated under reduced pressure to dryness, and 190 mg of Boc-3-(1-naphthyl)alanine was added to the residue, and dissolved in dry dimethyl formamide, and after adding thereto 98 mg of cyanophosphonic acid diethyl ester and 122 mg of triethyl amine under ice-cooling, the mixture was stirred for 30 minutes. The mixture was stirred overnight, and after adding thereto 50 ml of water, the mixture was extracted with 100 ml of ethyl acetate. The extract was washed with 5% NaHCO₃ aqueous solution and saturated NACl aqueous solution, and dried over anhydrous magnesium sulfate. The solvent was removed by distillation under reduced pressure to give colorless caramel of the crude product. This product was subjected to silica gel column chromatography (solvent:-chloroform:methanol=95:5) to purify the product, and colorless powder of the desired compound (170 mg).
Rf:=0.45 (chloroform:methanol=9:1)
MS (FAB): 678 (M++1)
IR$_{cm-1}$;$^{KBR}$ 3280, 2930, 1710, 1670

Examples 13–27

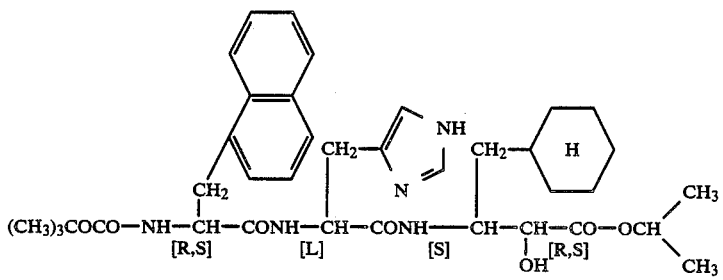

In similar manner to Example 12, the following compounds were obtained.

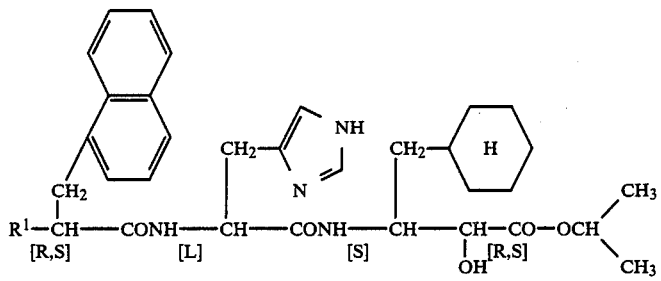

Example 13

(2RS,3S)-3-[N-[2-(1-naphthyl)methyl-3-(1-naphthyl)-propionyl]-L-histidyl]-amino-2-hydroxy-4-cyclohexyl butyric acid iso-propyl ester

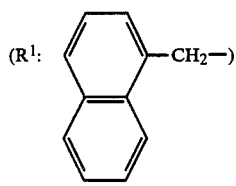

Example 14

(2RS,3S)-3-[N-[2-ethoxycarbonyl-3-(1-naphthyl)-propinyl]-L-histidyl]amino-2-hydroxy-4-cyclohexyl-butyric acid iso-propyl ester.

(R¹: CH₃CH₂OCO—)

Example 15

(2RS,3S)-3-[N-[2-(2-hydroxy-1(S)-methylethylcarbamoyl)-3-(1raphthyl)propionyl]-L-histidyl]amino-2-hydroxy-4-cyclohexylbutyric acid isopropyl ester.

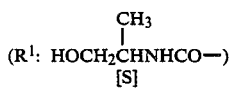

Example 16

(2RS,3S)-3-[N-[(2RS)-4-(3-thienyl)-2-(1-naphthylmethyl)-4-oxobutanoyl]-L-histidyl]amino-2-hydroxy-4-cyclohexylbutyric acid iso-propyl ester.

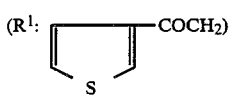

Example 17

(2RS,3S)-3-[N-[(2RS)-4-(2-thienyl)-2-(1-naphthylmethyl)-4-oxobutanoyl]-L-histidyl]amino-2-hydroxy-4-cyclohexylbutyric acid iso-propyl ester.

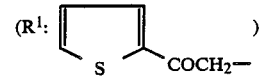

Rf = 0.59
MS (m/z): 687 (M⁺ + 1)
IR$\nu_{max}^{KBr}$ cm⁻¹: 2932, 1736, 1660

Example 18

(2RS,3R)-3-[N-[(2RS)-2-(N-morpholinocarbamoyl)-2-(1-naphthyl)propionyl]-L-histidyl]amino-2-hydroxy-4-cyclohexylbutyric acid iso-propyl ester.

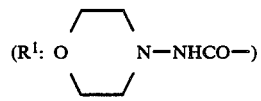

Rf: 0.45
MS (m/z): 691 (M⁺ + 1)
IR$\nu_{max}^{KBr}$ cm⁻¹: 2932, 1736, 1670

Example 19

(2RS,3S)-3-[N-[2-(RS)-6-methyl-2-(1-naphthylmethyl)-4-oxohexanoyl]-Lhistidyl]amino-2-hydroxy-4-cyclohexylbutyric acid iso-propyl ester.

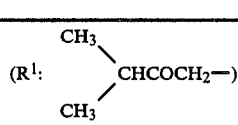

Rf = 0.54
MS (m/z): 647 (M⁺ + 1)
IR$\nu_{max}^{KBr}$ cm⁻¹: 2936, 1734, 1712, 1660

Example 20

(2RS,3S)-3-[N-2(RS)-4-(1,3-dioxolan-2-yl)-2-(1-naphthylmethyl)butanoyl]-L-histidyl]amino-2-hydroxy-4-cyclohexylbutyric acid iso-propyl ester.

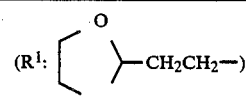

Rf = 0.67
MS (m/z): 663 (M⁺ + 1)
IR$\nu_{max}^{KBr}$ cm⁻¹: 2936, 1734, 1652

Example 21

(2RS,3S)-3-[N-[2(RS)-4-(1,3-dioxan-2-yl)-2-(1-naphthylmethyl) butanoyl]-L-histidyl]amino-2-hydroxy-4-cyclohexylbutyric acid iso-propyl ester

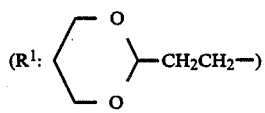

Rf = 0.45
MS (m/z): 676 (M⁺ + 1)
IR$\nu_{max}^{KBr}$ cm⁻¹: 2936, 1736, 1654

Example 22

(2RS,3S)-3-N-2-(RS)-4-phenyl-2-(1-naphthylmethyl)-4-oxobutanoyl]-L-histidyl]amino-2-hydroxy-4-cyclohexylbutyric acid iso-propyl ester

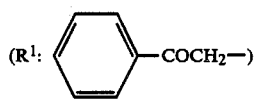

Rf = 0.63
MS (m/z): 681 (M⁺ + 1)
IR$\nu_{max}^{KBr}$ cm⁻¹: 2932, 1736, 1682

Example 23

(2RS,3S)-3-[N-[(2RS)-2-(1-naphthylmethyl)-3-(2-amino-thiazo-4-yl)propionyl]-L-histidyl]amino-2-hydroxy-4-cyclohexylbutyric acid iso-propyl ester.

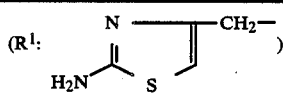

Rf = 0.34
MS (m/z): 675 (M⁺ + 1)
IR$\nu_{max}^{KBr}$ cm⁻¹: 2988, 1732, 1654

Example 24

(2R,3S)-3-[N-[(2RS)-2(1-naphthylmethyl)-4-pentinoyl]-L-histidyl]amino-2-hydroxy-4-cyclohexylbutyric acid iso-propyl ester.

( R¹: HC≡CCH₂—)

Rf = 0.54
MS (m/z): 601 (M⁺ + 1)
IR$\nu_{max}^{KBr}$ cm⁻¹: 3312, 1732, 1652

Example 25

(2RS,3S)-3-[N-(2(RS)-3-cyano-2-(1-naphthylmethyl)-propionyl]-L-histidyl]amino-2-hydroxy-4-cyclohexyl-butyric acid iso-propyl ester.

(R¹: NC CH₂—)

Rf = 0.63
MS (m/z): 602 (M⁺ + 1)
IR$\nu_{max}^{KBr}$ cm⁻¹: 2936, 2253, 1738, 1664

Example 26

(2RS,3S)-4-cyclohexyl-3-[N-4-cyclohexyl-1,4-dioxo-2-(1-naphthylmethyl)butyl]-L-histidyl]amino-2-hydroxybutyric acid iso-propyl ester.

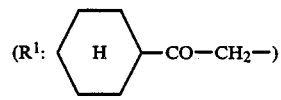

Rf = 0.17
MS (FAB): (m/z); 687 (M⁺ + 1)
IR$\nu_{max}^{KBr}$ cm⁻¹: 2936, 2856, 1734, 1662

Example 27

(2RS,3S}-4-cyclohexyl-3-[N-[1,4-dioxo-2-(1-naphthylmethyl)-4-(tetrahydropyran-4-yl)butyl]-L-histidyl]-amino-2-hydroxybutyric acid iso-propyl ester.

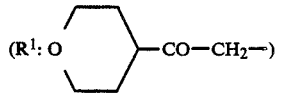

Rf = 0.08
MS (m/z): 689(M⁺ + 1)
IR$\nu_{max}^{KBr}$ cm⁻¹: 3336, 2936, 1734, 1664

Example 28

(2RS,3S)-4-cyclohexyl-2-hydroxy-3-[N-[3-(1-naphthylmethyl)-2-(R,S)-(2-phenetylaminocarbonyl)propionyl]-L-histidyl]aminobutyric acid iso-propyl ester.

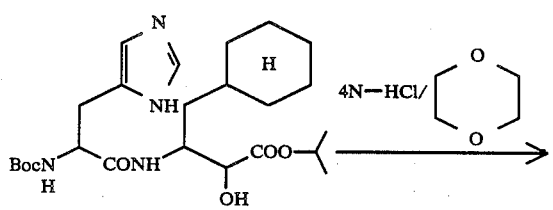

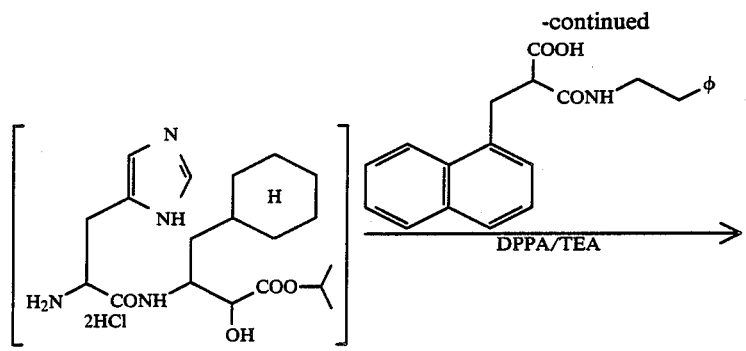
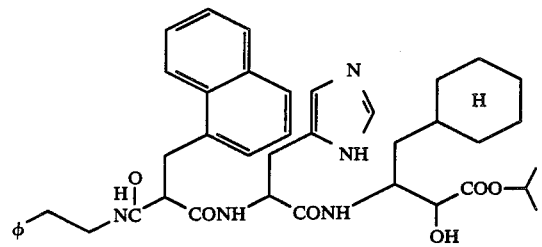
Rf = 0.36
MS: FAB(POS)(m/z)710(M+ + 1), 181
IRν $_{max}^{KBr}$ cm$^{-1}$: 3316, 2932, 2856, 1738
Example 29
(2RS,3S)-4-cyclohexyl-2-hydroxy-3-[N-[3-(1-naphthyl)-2-(R,S)-(1-naphthylaminocarbonyl)propionyl]-L-histidyl]-aminobutyric acid iso-propyl ester.
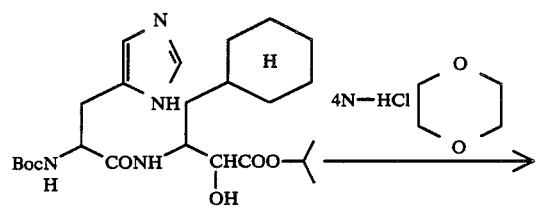
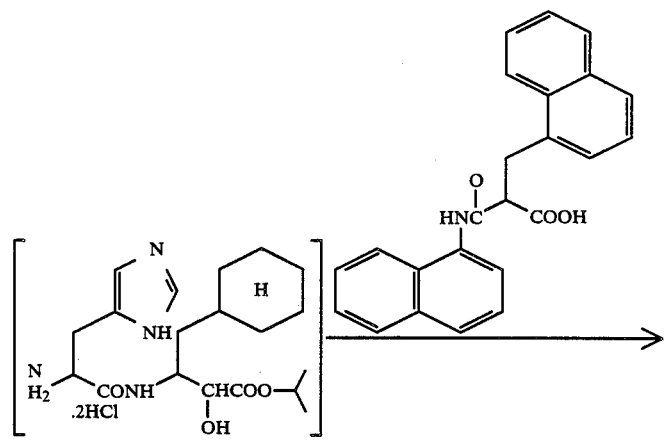

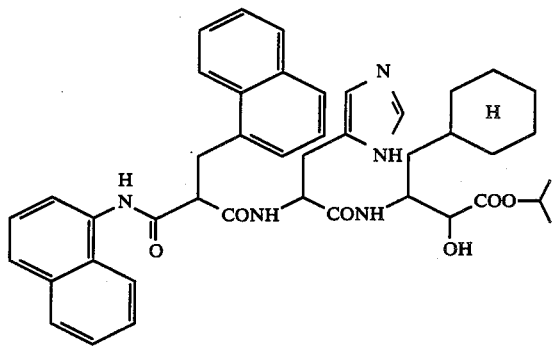
Rf = 0.40
MS: FAB(pos)(m/z)732(M$^+$ + 1), 449
IR$\nu_{max}^{KBr}$cm$^{-1}$: 2932, 1732, 1670
Example 30
(2RS,3S)-4-cyclohexyl-2-hydroxy-3-[N-[2(R,S)-cyclohexylidenem ethyl-3-(1-naphthyl)propionyl]-L-histidyl]-aminobutyric acid iso-propyl ester.
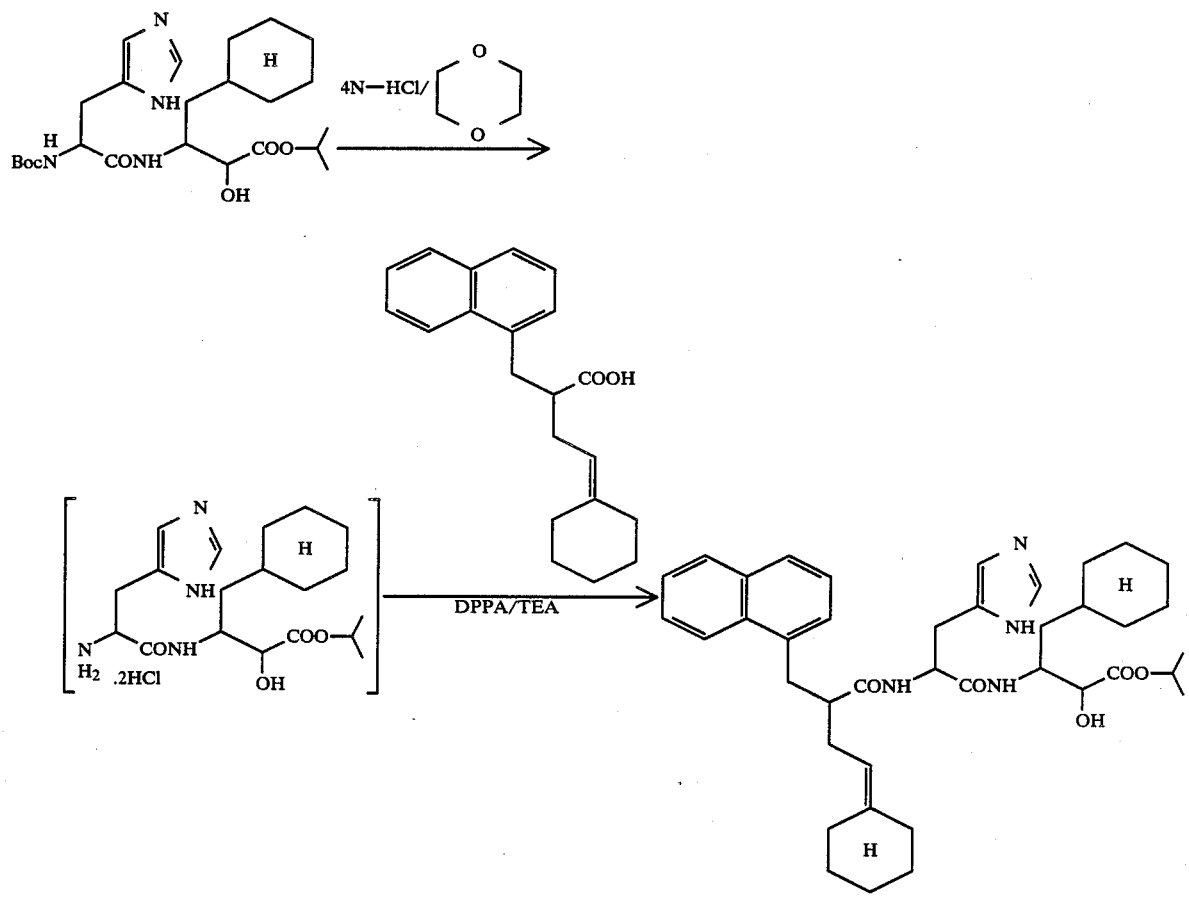
MS: FAB(pos);(m/z)671(M$^+$ + 1), 400
IR$\nu_{max}^{KBr}$cm$^{-1}$: 3320, 2936, 2856, 1738
Example 31
(2RS,3S)-4-cyclohexyl-3-[N-[4-cyclohexyl-4-hydroxy-2-(1-naphthyl-methyl)-1-oxobuty]]-L-histidyl-]amino-2-hydroxybutyric acid iso-propyl ester.

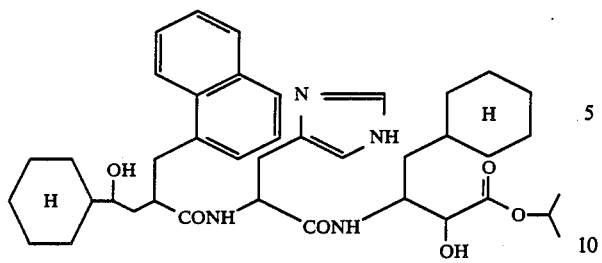

About 20 mg of sodium boron hydride was suspended in 3 ml of methanol, and the suspension was ice-cooled by ice bath. To the suspension was added about 20 mg of (2RS,3S)-4-cyclohexyl-3-[N-[4-cyclohexyl-1,4-dioxo-2-(1-naphthylmethyl)butyl]-L-histidyl]amino-2-hydroxybutyric acid iso-propyl ester, and the mixture was stirred for 40 minutes while ice-cooling. To the reaction mixture was added 1·0 ml of saturated aqueous NaHCO$_3$, and the mixture was extracted with ethyl acetate (20 ml×3). The organic layer was dried over anhydrous sodium sulfate, and the solvent was removed by distillation. The residue was dissolved in a small amount of ethyl acetate, and n-hexane was added thereto to give colorless crystal of the desired product. Yield: 17 mg. Rf=0.43 (chloroform:methanol-10:1)

MS:FAB (pos); (m/z) 689 (M$^+$ +1)

IR$\nu_{max}^{KBr}$ cm$^{-1}$: 3336, 2936, 1734, 1654

Example 32

In similar manner to Example 31, the following compound was obtained.

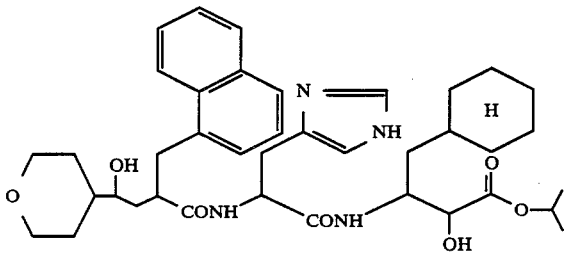

(2RS,3S)-4-cyclohexyl-2-hydroxy-3-[n-[4-hydroxy-2-(1-naphthylmethyl)-1-oxo-4-(tetrahydropyran-4-yl)butyl]-L-histidyl]-amino-butyric acid iso-propyl ester. Rf=0.29 (chloroform:methanol=10:1)

MS (m/z): 691 (M$^+$ +1)

IR$\nu_{max}^{KBr}$ cm$^{-1}$: 3420, 2936, 1734, 1654

Example 33

(2RS,3S)-3-[N-[2-(1-naphthylmethyl)-3-(morpholinocarbonyl)propionyl]-L-histidyl]amino-2-hydroxyhexanoic acid iso-propyl

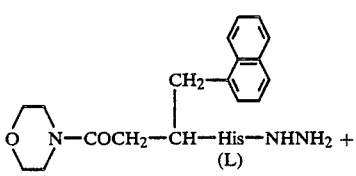

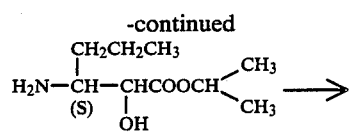

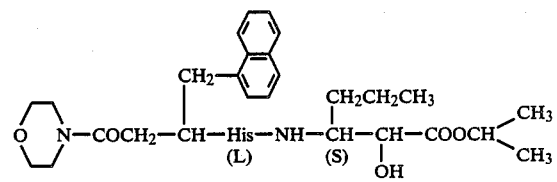

950 mg of N-[2-(1-naphthylmethyl)-3-(morpholinocarbonyl)propionyl]-L-histidine hydrozide is dissolved in 25 ml of dimethylformamide, and after adding thereto 1.6 ml of 4N HCl-dioxane (1.6 ml) and 0.46 ml of iso-amyl nitrite, the mixture was stirred for 30 minutes. The reaction mixture was cooled to −30° C., and neutralized with 0.92 ml of triethyl amine to give a solution of N-[2-(1-naphthylmethyl)-3-(morpholinocarbonyl)propionyl-L-histidine azide. This azide solution was added dropwise while cooling of a solution of 378 mg of (2RS,3S)-3-amino-2-hydroxyhexanoic acid iso-propyl ester in 12 ml of dimethylformamide, and the obtained mixture was stirred overnight at 4° C. To the reaction mixture was added aqueous saturated NaHCO$_3$, and the mixture was extracted with ethyl acetate. The organic layer was washed with saturated aqueous NaCl, and dried over anhydrous sodium sulfate. The solvent was removed by distillation under reduced pressure, and the residue was subjected to silica gel column chromatography and eluted by chloroform:methanol (95:5) for purification to give 160 mg of colorless powder of the desired compound. Rf:=0.19 (chloroform:methanol=95:5)

IR $_{max}^{KBr}$ cm$^{-1}$; 3290,2960,2930,1730,1640

MS (FAB); 636 (M$^+$+1)

Example 34

(2RS,3S)-3-[N-[2-(1-naphthylmethyl)-3-(morpholinocarbonyl)propionyl]-L-histidyl]amino-2-hydroxy-4-methylhexanoic acid iso-propyl ester.

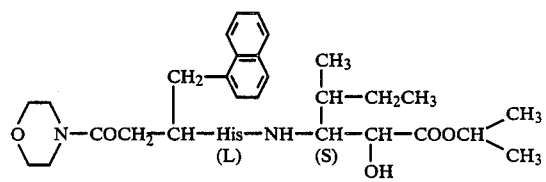

Using 624 mg of N-[2-(1-naphthylmethyl)-3-(morpholinocarbonyl)propionyl]-L-histidinehydrazide and 264 mg of (2RS,3S)-3-amino -2-hydroxy-4-methylhexanoic acid isopropyl ester as starting materials, the reaction was carried out in similar manner to Example 33, and the product was purified by silica gel column chromatography (eluting solution: chloroform:methanol=95:5) to give 30 mg of the desired compound.

Rf:=0.29 (chloroform:methanol=9:1).

IR $_{max}^{KBr}$ cm$^{-1}$; 3300, 2970, 1730, 1640

MS (FAB): 650 (M$^+$ +1)

Examples 35-38

In similar manner to Example 33, the following compounds were obtained.

Example 35

(2RS,3S)-3-[N-[2-(1-naphthylmethyl)-3-(morpholinocarbonyl) propionyl]-L-histidyl]amino-2-hydroxy-4-methylvaleric acid iso-propyl ester.

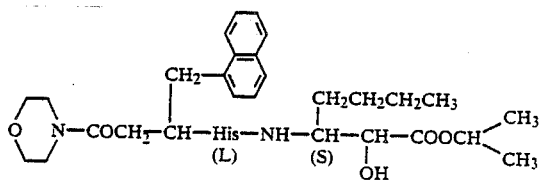

i) m.p. ; 100 ~ 101 °C
ii) Rf ; 0.21
(クロロホルム : メタノール = 95 : 5)
iii) IR $_{max}^{KBr}$ cm$^{-1}$ ; 3300, 2970, 1730, 1660, 1630
MS (FAB) ; 636 (M$^+$+1)

Example 36

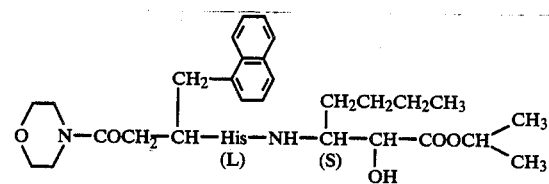

(2RS,3S)-3-[N-[2-(1-naphthylmethyl)-3-(morpholinocarbonyl) propionyl-L-histidyl]amino-2-hydroxy-heptanoic acid iso-propyl ester.
m.p.; 85°~87° C.
Rf; 0.18 (クロロホルム : メタノール = 95: 5)
IR $_{max}^{KBr}$ cm$^{-1}$; 3290, 2940, 1735, 1640
MS (FAS) ; 650 (M+1)

Example 37

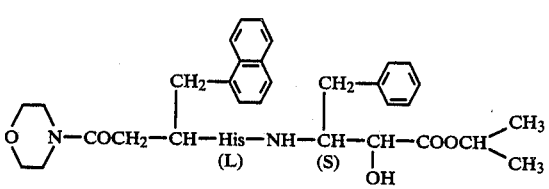

(2RS,3S)-3-[N-[2-(1-naphthylmethyl)-3-(morpholinocarbonyl) propionyl]-L-histidyl]amino-2-hydroxy-4-phenylbutyric acid iso-propyl ester.
IR $_{max}^{KBr}$ cm$^{-1}$; 1738, 1646, 1112
MS (FAB); 684 (M+ +1)

Example 38

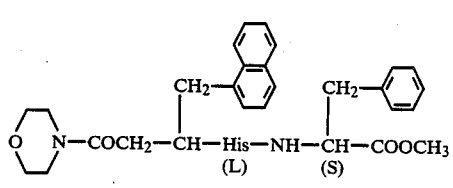

(2RS,3S)-3-[N-[2-(1-naphthylmethyl)-3-(morpholinocarbonyl)propionyl]-L-histidyl]amino-2-hydroxy-4-phenylbutyric acid methyl ester.
IR $_{max}^{KBr}$ cm$^{-1}$; 1748, 1646, 1116
MS (FAS); 656 (M+ +1)

Example 39

(2RS,3S)-3-[N-[4-(p-fluorophenoxy)-2-(1-naphthylmethyl)-butyryl]-L-histidyl]amino-2-hydroxy-4-cyclohexylbutyric acid iso-propyl ester.

(a) N-[4-(p-fluorophenoxy)-2-(1-naphthylmethyl)-butyryl]-L-histidine methyl ester. 20 ml of dimethylformamide was added to 1.5 g of 4-(p-fluorophenoxy)-2-(1-naphthylmethyl)-butyric acid, 0.6 g of 1-hydroxybenzotriazole and 1.1 g of L-histidine 2HCl salt, and the mixture was neutralized with 1.3 ml of triethylamine, and after adding thereto, 1.0 g of N,N'-dicyclohexylcarbodiimide, the mixture was stirred overnight at room temperature. The insoluble matter was removed, and dimethylformamide was removed by distillation under reduced pressure. To the residue was added 100 ml of methylene chloride and the mixture was washed with saturated aqueous NaHCO$_3$ and water, and the organic layer was dried over anhydrous magnesium sulfate followed by being subjected to silica gel column chromatography for purification. 1.7 g of white powder of the aimed compound was obtained.
Melting point: 65°–69° C.
IR (cm$^{-1}$): 1746, 1656, 1508, 1250
MS: 490 (M+ +1)

(b) N-[4-(p-fluorophenoxy)-2-(1-naphthylmethyl)-butyryl]-L-histidine hydrazide. 1.7 g of N-[4-(p-fluorophenoxy)-2-(1-naphthylmethyl)-butyryl]-L-histidine obtained above (a) was dissolved in 40 ml of methanol, and after adding thereto 0.6 ml of hydrazine hydrate, the mixture was stirred overnight at room temperature. The reaction solution was concentrated under reduced pressure, and after adding to the residue 100 ml of ethyl acetate, the mixture was washed with water, dried over magnesium sulfate, and concentrated under reduced pressure to give white powder of the desired compound (1.5g).
Melting point: 87°–91° C.
IR (cm$^{-1}$): 3292, 1654, 1508, 1250

(c) (2RS,3S)-3-[N-[4-(p-fluorophenoxy)-2-(1-naphthylmethyl)butyryl]-L-histidyl]amino-2-hydroxy-4-cyclohexylbutyric acid iso-propyl ester. 489 mg of N-[p-fluorophenoxy)-2-(1-naphthylmethyl)-butyryl]-L-histidine hydrazide was dissolved in 18 ml of dimethylformamide, and after adding thereto at −40° C., 0.84 ml of 4N HCl-dioxane and then 0.2 ml of iso-amyl nitrite, the mixture was stirred for 30 minutes at −20° C. − −30° C. The reaction mixture was cooled to −40° C., and after adding thereto 0.34 ml of N-methylmorpholine and then 243 mg of (2RS,3S)-3-amino-2-hydroxy-4-cyclohexylbutyric acid iso-propyl ester, the reaction mixture was stirred at 0°-5° C. overnight. The reaction mixture was poured into 100 ml of ice water, extracted with methylene chloride, and washed with saturated NaHCO$_3$ aqueous solution and water, and then dried over anhydrous magnesium sulfate followed by being subjected to silica gel column chromatography for purification. 300 mg of whiter powder of the desired compound (rf 0.52, 300 mg) was obtained. Rf value: thin layer column chromatography (Merck, precoat plate silica gel 60F$_{254}$), eluting solution (chloroform-methanol=5:1).

Example 40

(2RS,3S)-3-[N-[2-(1-naphthylmethyl)-3-morpholinocarbonyl)-propionyl]-L-histidyl]amino-2-hydroxy-4-cyclohexylbutyric acid iso-propyl ester. 480 mg of N-[2-(1-naphthylmethyl)-3-(morpholinocarbonyl)-propionyl]-L-histidine hydrazide was dissolved in 13 ml of dimethylformamide, and after adding thereto, at −20° C., 0.8 ml of 4N HCl-dioxane and 0.17 ml of iso-amyl nitrite, the mixture was stirred for 30 minutes. The reaction mixture was cooled to −30° C., and neutralized with triethylamine to give a solution of N-[2-(1-naphthylmethyl)-3-(morpholinocarbonyl)propionyl]-L-histidine azide. This azide solution was added dropwise under ice-cooling to a solution of 243 mg of (2RS,3S)-3-amino-2-hydroxy-4-cyclohexylbutyric acid iso-propyl ester in 25 ml of dimethylformamide, and the mixture was stirred overnight at 4° C. To the reaction solution was added saturated aqueous NaHCO₃, and the mixture was extracted with ethyl acetate. The organic layer was washed with saturated aqueous NaCl, and dried over anhydrous sodium sulfate. The solvent was removed by distillation under reduced pressure, and the residue was subjected to silica gel column chromatography and eluted by chloroform-methanol (95:5) for purification to give 350 mg of colorless powder of the desired compound (Rf=0.34, 350 mg).

Melting point: 103°–107° C.
MS(FAB): 690 (M+ +1)

Example 41

(2RS,3S)-3-[N-[2-(1-naphthylmethyl)-3-(morpholinocarbonyl)propionyl]-L-histidyl]amino-2-hydroxy-4-cyclohexylbutyric acid methyl ester. Using N-[2-(1-naphthylmethyl)-3-(morpholinocarbonyl)-propionyl]-L-histidine hydrazide (480 mg) and 243 mg of (2RS,3S)-3-amino-2-hydroxy-4-cyclohexylbutyric acid methyl ester, in similar manner to Example 40, the reaction was carried out and the product was purified by silica gel column chromatograph (eluting solution:- chloroform-methanol=95:5) to give 150 mg of colorless powder of the desired compound (rf=0.64).

Melting point: 83°–87° C.
MS(FAB): 662 (M+ +1)

Example 42

N-(2-benzyl-3-phenylpropionyl)-L-histidyl-(2RS,3S)-3-amino-2-hydroxy-4-cyclohexylbutyric acid iso-propyl ester.

(a) N-tert-butoxycarbonyl-L-histidyl-(2RS,3S)-3-amino-2-hydroxy-4-cyclohexylbutryic acid iso-propyl ester. 2.44 g of (2RS,3S)-3-amino-2-hydroxy-4-cyclohexylbutryic acid iso-propyl ester and 2.75 g of N-tert-butoxycarbonyl-L-histidine was dissolved in 130 ml of dimethylformamide, and after adding thereto, under ice-cooling, 1.85 g of cyanophosphoric acid diethyl ester and 2.17 g of triethylamine, the mixture was stirred for 30 minutes under ice-cooling, and then at room temperature for 4 hours. The solvent was removed by distillation under reduced pressure and water was added to the residue. The mixture was extracted with ethyl acetate and the organic layer was washed with 10% aqueous citric acid, saturated NaHCO₃ aqueous solution and saturated aqueous NaCl, and then dried over anhydrous sodium sulfate. The solvent was removed by distillation under reduced pressure and the residue was subjected to column chromatography (silica gel), and eluted by chloroform-methanol (97:3) for purification to give a powder of the desired compound (700 mg). NMR (CDCl₃) ppm: 0.6–2.0 (m, 33H), 219–3.1(m,1H); 4.08(d,1H, J–3.1Hz), 4.1–4.6(m,1H), 4.9–5.2(m,1H); and 5.6–5.9(m,1H), 6.84 (sl1H), 7.56(s,1H).

MS: 480 (M+)

(b) N-(2-benzyl-3-phenylpropionyl)-L-histidyl-(2RS,3S)-3-amino-2-hydroxy-4-cyclohexylbutyric acid iso-propyl ester. 120 mg of N-tert-butoxycarbonyl-L-histidyl-(2RS,3S)-3-amino-2-hydroxy-4-cyclohexylbutyric acid iso-propyl ester was dissolved in 60 ml of 4N HCl-dioxane, and the mixture was stirred for 40 minutes at room temperature. The solvent was removed by distillation under reduced pressure to dryness, and after adding thereto 60 mg of 2-benzyl-3-phenylpropionic acid, the mixture was dissolved in 3 ml of dimethyl-formamide. After adding thereto, under ice-cooling, 41 mg of cyanophosphoric acid diethyl ester and then 53 mg of triethylamine dropwise, the mixture was stirred for 30 minutes under ice-cooling and then overnight at room temperature. The solvent was removed by distillation and water was added to the residue. The obtained mixture was extracted with ethyl acetate and the organic layer was washed with 5% HCl, saturated NaHCO₃ aqueous solution, and then saturated aqueous NaCl, and dried over anhydrous magnesium sulfate. The solvent was removed by distillation under reduced pressure, and tee residue was subjected to column chromatography (silica gel) and eluted with chloroform-methanol (95:5) for purification to give 70 mg of the desired compound as a colorless powder (rf=0.61).

Melting point: 91°–94° C.
MS(FAB): 503 (M+ +1)

Example 43

In similar way to Example 1, (3S)-3-(N-t-butoxycarbonyl-L-phenylalanyl-L-histidylamino)-5-methyl-1-nitro-2-hexanol was prepared.

Examples 44–51

In similar way to Example 8, the following compounds were prepared:
(3S)-4-cyclohexyl-3-[(N-[1,4-dioxo-4-morpholino-2-(1-naphthylmethyl)butyl]-L-histidyl]amino]-1-(2-thiazolylthio)-2-butanol; (3S)-4-cyclohexyl-3-[(N-[1,4-dioxo-4-morpholino-2-(1-naphthylmethyl)butyl]-L-histidyl]amino]-1-[(5-methyl-1,3,4-thiadiazol-2-yl)thio]-2-butanol; (3S0-4-cyclohexyl-3-[(N-[1,4-dioxo-4-morpholino-2-(1-naphthylmethyl)butyl]-L-histidinyl]amino]-1-(2-pyrimidinylthio)-2-butanol; (3S)-4-cyclohexyl-3-[(N-[1,4-dioxo-4-morpholino-2-(1-naphthylmethyl)butyl]-L-histidyl]amino]-1-(1,2,3-thiadiazol-5-ylthio)-2-butanol; (3S)-cyclohexyl-3-[(N-[1,4-dioxy-2-(1-naphthylmethyl)-4-(3-thienyl)butyl]-L-histidyl]amino]-1-(1-methyl-5-tetrazolyl)-2-butanol; (3S)-4-cyclohexyl-3-[(N-[1,4-dioxo-4-morpholino)-2-(1-naphthyl)butyl]-L-histidyl]amino]-1-[(1-ethyl-5-tetrazolyl)-thio]-2-butanol; (3S)-4-cyclohexyl-3-[(N-1,4-dioxo-4-morpholino)-2-(1-naphthylmethyl)butyl]-L-histidyl]amino]-1-[(1-methyl-5-tetrazolylsulfonyl]-2-butanol; and (3S)-4-cyclohexyl-3-[(N-[1,4-dioxo-4-morpholino)-2-(1-naphthylmethyl)butyl]-L-histidyl]amino]-1-nitro-2-butanol.

Examples 52–54

In similar way to Example 9, the following compounds were prepared:

(3S)-1-(2-benzthiazolylthio)-3-[(N-t-butoxycarbonyl-L-phenylalanyl-L-histidyl)amino]-4-cyclohexyl-2-butanol;

(3S)-3-[(N-t-butoxycarbonyl-L-phenylalanyl-L-histidyl)amino)]-4-cyclohexyl-1-[(5-hydroxymethyl-1,3,4,-thiadiazol-2-yl)thio]-2-butanol; and (3S)-3-[(N-butoxycarbonyl-L-phenylalanyl-L-histidyl)-amino)]-4-cyclohexyl-1-nitro-2-butanol.

Example 55

(3S)-3-[N-(t-butyloxycarbonyl-1-phenylalanyl-L-histidyl)-N-methyl]amino-4-cyclohexyl-2-hydroxybutanoin acid iso-propyl ester.

Example 56

(3S)-3-[(N-[3-(morpholino)carbonyl)-2-(1-naphthylmethyl)-propionyl]-L-histidyl]-N-methyl]amino)-4-cyclohexyl-2-hydroxybutanoic acid iso-propyl ester.

Example 57

Iso-propyl (3S)-3-(t-butyloxycarbonyl-L-phenylalanyl-L-histidyl)amino-2-cyclohexyl-2-hydroxybutyrate. 0.48 g of iso-propyl (3S)-3-(5-butyloxycarbonyl-L-histidyl)-amino-2-cyclohexyl-2-hydroxybutyrate was dissolved in 10 ml of 4N HCl-dioxane and after stirring the solution at room temperature for 1 hour, the solvent was removed by distillation and the residue was dissolved in 4 ml of dimethylformamide. After cooling the solution with ice, 0.52 ml of triethylamine, 0.29 g of t-butyloxycarbonyl-phenylalanine, and 0.26 g of diphenylphosphatidylazide were added successively to the solution. After stirring the mixture at room temperature, 30 ml of saturated aqueous NaHCO3 was added thereto, and the obtained mixture was extracted with ethyl acetate (50 ml×3). The organic layer was washed with 30 ml of water, dried over anhydrous sodium sulfate, and then the solvent was removed by distillation. The residue was subjected to silica-gel column chromatography (CHCl3:methanol=100:1–10:1) to purify the product. The product was crystallized from ether-n-hexane to give a white powder of the desired compound (505 mg).

Rf: 0.33 (chloroform:methanol=10:1)
MS(FAB): 628 (M+ +1)
IR (KBr) (cm$^{-1}$): 3432, 2936, 1724, 1662

Reference Example 57

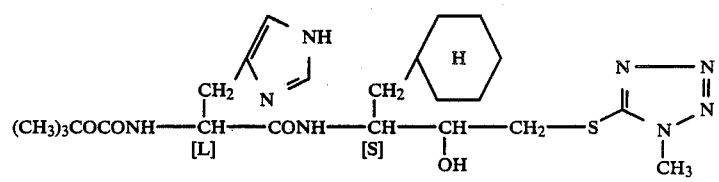

(2RS,3S)-3-N-[(N$^\alpha$-1-butoxycarbonyl-L-histidyl)amino-4-cyclohexyl-1-(1-methyl-5-tetrazolylthio)-2-butanol. To 1 g of 3-N-t-butoxycarbonylamino-4-cyclohexyl-1-(1-methyl-5-tetrazolylthio)-2-butanol (2.6 millimole) was added 15 ml of 4N-HCl/dioxane, and after stirring the mixture at room temperature for 1 hour, the mixture was concentrated under reduced pressure to dryness. To the residue was added 663 mg of N-t-butoxycarbonyl-L-histidine and 350 mg of 1-hydroxybenzotriazole and 20 ml of dimethylformamide. The mixture was stirred under ice-cooling, and after adding thereto 0.37 ml of triethylamine and 600 mg of N,N'-dicyclohexylcarbodiimide, the mixture was stirred at room temperature overnight. The insoluble matter was removed by filtration, and after adding thereto 100 ml of ethyl acetate, the mixture was washed with aqueous NaHCO3 and water, dried over magnesium sulfate, and concentrated. To the residue was added ether-n-hexane and 520 mg of a white powder of the desired compound.

Rf=0.45 (chloroform:methanol=5:1)
MS(m/z):523 (M+ +1), 423
IR(KBr)cm$^{-1}$: 3364, 2936, 1698, 1646, 1526, 1172

Example 58

In similar way to Example 33, (2RS,3S)-3-[N-[2-(1-naphyhylmethyl)-3-morpholinocarbonyl)propionyl]-L-histidyl]amino-5,5-dimethyl-2-hydroxyhexanoic acid iso-propyl ester was obtained.

Melting point: 101°–104° C.

Summary of Working Examples

| R$_1$ | R$_2$ | R$_3$ | R$_4$ |
|---|---|---|---|
| F-C6H4-OCH2CH2 | naphthyl | cyclohexyl | COOCH(CH3)2 |
| morpholino-N-CO-CH2 | naphthyl | cyclohexyl | COOCH(CH3)2 |
| morpholino-N-CO-CH2 | naphthyl | H (cyclohexyl) | COOCH3 |

-continued

| R₁ | R₂ | R₃ | R₄ |
|---|---|---|---|
| PhCH₂– (benzyl) | phenyl | H (cyclohexyl) | COOCH(CH₃)₂ |
| morpholine-N-CO-CH₂– | 1-naphthyl | –CH₂CH₃ | COOCH(CH₃)₂ |
| morpholine-N-CO-CH₂– | 1-naphthyl | (–CH₂–R₃) –CH(CH₃)CH₂CH₃ | COOCH(CH₃)₂ |
| morpholine-N-CO-CH₂– | 1-naphthyl | (–CH₂–R₃) –CH(CH₃)₂ | COOCH(CH₃)₂ |
| morpholine-N-CO-CH₂– | 1-naphthyl | –CH₂CH₂CH₃ | COOCH(CH₃)₂ |
| morpholine-N-CO-CH₂– | 1-naphthyl | phenyl | COOCH(CH₃)₂ |
| morpholine-N-CO-CH₂– | 1-naphthyl | phenyl | –COOCH₃ |
| (CH₃)₃COCONH– | 1-naphthyl | H (cyclohexyl) | COOCH(CH₃)₂ |
| 1-methylnaphthyl | " | " | " |
| CH₃CH₂OCO– | " | " | " |
| HOCH₂CH(CH₃)NHCO– | " | " | " |
| 2-thienyl-COCH₂– | " | " | " |

| R₁ | R₂ | R₃ | R₄ |
|---|---|---|---|
| | " | " | " |
| ⟨thiophene⟩-COCH₂— | " | " | " |
| ⟨morpholine⟩N—NHCO— | " | " | " |
| (CH₃)₂CHCOCH₂— | " | " | " |
| ⟨1,3-dioxolane⟩-CH₂—CH₂— | " | " | " |
| ⟨1,3-dioxane⟩-CH₂—CH₂— | " | " | " |
| C₆H₅-COCH₂— | " | " | " |
| ⟨2-amino-thiazol-4-yl⟩-CH₂— | " | " | " |
| HC≡C—CH₂— | " | " | " |
| NCCH₂— | " | " | " |
| cyclohexyl-CO—CH₂— | " | " | " |
| ⟨tetrahydropyran-3-yl⟩-COCH₂— | " | " | " |
| C₆H₅-CH₂CH₂NHCO— | " | " | " |
| ⟨pentadienyl⟩-NHCO— | " | " | " |
| cyclohexyl-CH—CH₂— | " | " | " |

-continued

| R₁ | R₂ | R₃ | R₄ |
|---|---|---|---|
| cyclohexyl-CH(OH)-CH₂- | " | " | " |
| (CH₃)₃COCONH- | phenyl | -CH(CH₃)₂ | CH₂-S-TZ |
| (CH₃)₃COCONH- | phenyl | -CH(CH₃)₂ | CH₂-S-C(=N-CH=CH-S) (thiazoline) |
| (CH₃)₃COCONH | phenyl | -CH(CH₃)₂ | CH₂-S-C(=N-C(CH₃)=CH-O) (oxazoline) |
| (CH₃)₃COCONH | phenyl | -CH(CH₃)₂ | CH₂-S-C(=N-N=C(CH₃)-S) (thiadiazoline) |
| (CH₃)₃COCONH | phenyl | -CH(CH₃)₂ | CH₂-S-C(=N-CH=CH-N(CH₃)) (N-methylimidazoline) |
| (CH₃)₃COCONH | phenyl | -CH(CH₃)₂ | CH₂-S-C(=N-CH=CH-S) (thiazoline) |
| morpholino-N-CO-CH₂ | naphthyl | cyclohexyl | CH₂-S-TZ |
| tetrahydropyran-4-yl-CO-CH₂ | naphthyl | cyclohexyl | CH₂-S-TZ |
| (CH₃)₃COCONH | phenyl | cyclohexyl | CH₂-S-TZ |
| (CH₃)₃COCONH | phenyl | cyclohexyl | CH₂-S-TZ(CH₂CONH₂) |

-continued

| R₁ | R₂ | R₃ | R₄ |
|---|---|---|---|
| (CH₃)₃COCONH | phenyl | H | CH₂—S—(thiazoline) |
| (CH₃)₃COCONH | phenyl | H | CH₂—S—(benzothiazole) |
| (CH₃)₃COCONH | phenyl | H | CH₂—S—C(=N—N)—OH (thiadiazole-OH) |
| morpholino-N—CO—CH₂ | naphthyl | H | CH₂—S—(thiazoline) |
| morpholino-N—CO—CH₂ | naphthyl | H | CH₂—S—C(=N—N—CH₃)S (thiadiazole-CH₃) |
| morpholino-N—CO—CH₂ | naphthyl | H | CH₂—S—(pyrimidine) |
| morpholino-N—CO—CH₂ | naphthyl | H | CH₂—S—(thiadiazole) |
| thienyl—COCH₂ | naphthyl | H | CH₂S—TZ |
| (CH₃)₃COCONH | phenyl | —N(CH₃)— | COOCH(CH₃)₂ |
| (CH₃)₃COCONH | phenyl | H | COOCH(CH₃)₂ |
| morpholino-N—COCH₂ | naphthyl | —N(CH₃)— | COOCH(CH₃)₂ |

The compound of Example 55 was prepared as follows:

0.21 g of t-butyloxycarbonyl-L-phenylalanyl-L-histidylhydrazide was dissolved in 3 ml of dimethylformamide, and after cooling the mixture to −60° C. and adding thereto 0.43 ml of 4N-HCl/1,4-dioxane and 0.10 ml of isoamyl nitrite, the mixture was stirred for 30 minutes at −20° C. The reaction mixture was cooled to −60° C., and after adding thereto 0.30 ml of N-methylmorpholine, 5 ml of dimethylformamide solution containing (3S0-4-cyclohexyl-2-hydroxy-3-methylaminobutanoic acid iso-propyl ester HCl salt, successively, the mixture was stirred for 1 day at 4° C. To the reaction solution was added 50 ml of saturated aqueous NaHCO₃, and the mixture was extracted with ethyl acetate (100 ml×3). The organic layer was washed with 50 ml of water and saturated aqueous NaCl, successively, and then was dried over anhydrous sodium sulfate, and the solvent was removed by distillation. The residue was subjected to column chromatography (silica gel, chloroform:methanol=100:1–10:1) to purify the product. By treatment with ether-n-hexane, 0.12 g of white powder of the desired compound was obtained.

Rf: 0.39 (chloroform:methanol=10:1)

The compound of Example 56 was obtained as follows:

100 mg of (3S)-3-[N-(t-butyloxycarbonyl-L-histidyl)-N-methyl]amino-4-cyclohexyl-2-hydroxybutanoic acid isopropyl ester was dissolved in 3 ml of 4N-HCl/dioxane, and the solution was removed by distillation, and the residue was dissolved in 3 ml of dimethylformamide. The solution was cooled with ice, and after adding thereto 0.11 ml of triethylamine, 76 mg of 3-(morpholinocarbonyl)-2-(1-naphthylmethyl)propionic acid and 0.05 ml of diphenylphosphatidyl azide, the mixture was stirred for 1 day at room temperature. To the mixture was added 30 ml of saturated aqueous NaHCO₃, and the mixture was extracted with ethyl acetate (50 ml×3), and the organic layer was washed with 30 ml of water, dried over anhydrous sodium sulfate, and then the solvent was removed by distillation. The residue was subjected to silica gel column chromatography (chloroform:methanol=100:1–20:1) to purify the product. By treating ether-n-hexane, 50 mg of a whiter powder of the desired compound was obtained. Rf: 0.44 (chloroform:methanol=10:1).

What is claimed is:

1. A compound of the formula (I)

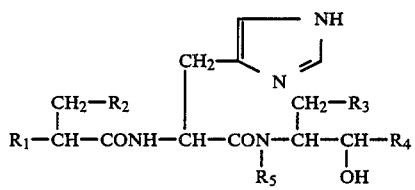

wherein $R_1$ is a lower alkoxycarbonyl group, a lower alkoxycarbonylamino group, a group of the formula: —(CH₂)ₙ—A—$R^a$ wherein n is an integer of 1 or 2; A is a single bond, a lower alkylene group which may be substituted by a hydroxy group (s), or a carbonyl group, $R^a$ is a cyano group, a lower alkyl group, a lower alkynyl group, a cycloalkyl, a cylcoalkylidene group, a hydrocarbyl aryl group, an aryloxy group which may be substituted by at least one halogen atom, or a 5 or 6 membered heterocyclic ring group wherein the heteroatoms are at least one of oxygen, nitrogen and sulfur, which groups may be substituted by at least on amino group, or a group of the formula: —CONH—B—$R^b$ wherein B is a single bond, or a lower alkylene; $R^b$ is a hydroxyl group, an aryl group, or a heterocyclic group; $R_2$ is a phenyl group or a naphthyl group; $R_3$ is a lower alkyl group, cyclohexyl group, or a phenyl group; $R_4$ is a nitromethyl group, a group of the formula: —COO$R^c$ wherein $R^c$ is a lower alkyl group; or a group of the formula:

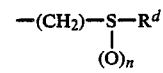

wherein n is zero or an integer of 1 or 2; $R^d$ is a 5 or 6 membered heterocyclic ring group wherein the heteroatoms are at least one of oxygen, nitrogen and sulfur which groups may be substituted by at least one lower alkyl group, a carbamoyl-lower-alkyl group (s), or a hydroxy-lower-alkyl group; and $R^5$ is a hydrogen atom or a lower alkyl group.

2. A compound according to claim 1, which is (2RS,3S)-3-(N-(2-(1-naphthylmethyl)-3-(morpholinocarbonyl)-propionyl)-L-histidyl)amino-2-hydroxy-4-cyclohexylbutyric acid isopropyl ester.

3. A compound according to claim 1, which is (2RS,3S)-3-(N-(1,4-dioxo-4-morpholine-2-(1-naphthylmethyl)-butyl-L-histidylamino)-4-cyclohexyl-1-(1-methyl-5-tetrazolylthio)-2-butanol.

4. A compound according to claim 1 which is (2RS,3S)-3-(N-t-butoxycarbonyl-L-phenylalanyl-L-histidyl-amino)-4-cyclohexyl-1-(1-methyl-5-tetrazolylthio)-2-butanol.

5. A pharmaceutical composition useful as an anti-hypertensive agent comprised of an anti-hypertensive effective amount of the compound of claim 1 and a pharmaceutically acceptable carrier.

6. The pharmaceutical composition of claim 5 wherein said compound is (2RS,3S)—
3-(N-(2-(1-naphthylmethyl)-3-(morpholinocarbonyl)-propionyl)-L-histidyl) amino-2-hydroxy-4-cyclohexyl-butyric acid isopropyl ester.

7. The pharmaceutical composition of claim 5 wherein said compound is (2RS,3S)
-3-(N-(1,4-dioxo-4-morpholino-2-(1-naphthylmethyl)-butyl-L-histidylamino)-4-cyclohexyl-1-(1-methyl-5-tetrazolylthio)-2-butanol.

8. The pharmaceutical composition of claim 5 wherein said compound is (2RS,3S)—
3-(N-t-butoxycarbonyl-L-phenylalanyl-L-histidyl-amino)-4-cyclohexyl-1-(1-methyl-5-tetrazolylthio)-2-butanol.

9. A method of producing an anti-hypertensive activity in a subject, which comprises administering to said subject an anti-hypertensive effective amount of the pharmaceutical composition of claim 5.

10. A method of producing a renin-inhibitor activity in a subject which comprises administering to said subject a renin-inhibitor effective amount of the pharmaceutical composition of claim 5.

* * * * *